US012797399B2

(12) United States Patent
Yu et al.

(10) Patent No.: US 12,797,399 B2
(45) Date of Patent: Nov. 17, 2026

(54) LYOPHILIZED FORMULATION SOLUTION AND LYOPHILIZED FORMULATION, AND METHOD AND USE THEREOF

(71) Applicant: ASCENTAWITS PHARMACEUTICALS, LTD., Shenzhen (CN)

(72) Inventors: Jibing Yu, Shenzhen (CN); Jianxin Duan, Shenzhen (CN); Xiaohong Cai, Shenzhen (CN); Qilong Fang, Shenzhen (CN); Guangbin Shen, Shenzhen (CN)

(73) Assignee: Ascentawits Pharmaceuticals, Ltd., Guangdong (CN)

( * ) Notice: Subject to any disclaimer, the term of this patent is extended or adjusted under 35 U.S.C. 154(b) by 381 days.

(21) Appl. No.: 18/686,722

(22) PCT Filed: Aug. 26, 2022

(86) PCT No.: PCT/CN2022/115176

§ 371 (c)(1),
(2) Date: Feb. 26, 2024

(87) PCT Pub. No.: WO2023/025291

PCT Pub. Date: Mar. 2, 2023

(65) Prior Publication Data

US 2024/0366640 A1 Nov. 7, 2024

(30) Foreign Application Priority Data

Aug. 27, 2021 (CN) ......................... 202110996128.8

(51) Int. Cl.

| | |
|---|---|
| ***A61K 31/675*** | (2006.01) |
| ***A61K 9/08*** | (2006.01) |
| ***A61K 9/16*** | (2006.01) |
| ***A61K 9/19*** | (2006.01) |

(52) U.S. Cl.

CPC .............. *A61K 31/675* (2013.01); *A61K 9/08* (2013.01); *A61K 9/1611* (2013.01); *A61K 9/1617* (2013.01); *A61K 9/1623* (2013.01); *A61K 9/19* (2013.01)

(58) Field of Classification Search

CPC ...... A61K 31/675; A61K 9/08; A61K 9/1611; A61K 9/1617; A61K 9/1623; A61K 9/19

See application file for complete search history.

(56) References Cited

U.S. PATENT DOCUMENTS

| | | | | |
|---|---|---|---|---|
| 2010/0183742 A1* | 7/2010 | Ammons ................ | A61P 35/00 424/649 |
| 2013/0202716 A1 | 8/2013 | Curd et al. | |
| 2014/0105824 A1 | 4/2014 | Shepard et al. | |

FOREIGN PATENT DOCUMENTS

| | | |
|---|---|---|
| WO | 2004087075 A2 | 10/2004 |
| WO | 2007002931 A2 | 1/2007 |
| WO | 2008151253 A2 | 12/2008 |
| WO | 2009018163 A1 | 2/2009 |
| WO | 2009033165 A2 | 3/2009 |
| WO | 2012006032 A2 | 1/2012 |
| WO | 2012009288 A2 | 1/2012 |
| WO | 2012135757 A2 | 10/2012 |
| WO | 2012142520 A1 | 10/2012 |
| WO | 2012145684 A2 | 10/2012 |
| WO | 2013096684 A2 | 6/2013 |
| WO | 2013096687 A1 | 6/2013 |
| WO | 2013116385 A1 | 8/2013 |
| WO | 2013126539 A2 | 8/2013 |
| WO | 2013177633 A2 | 12/2013 |
| WO | 2014169035 A1 | 10/2014 |
| WO | 2015013448 A1 | 1/2015 |
| WO | 2015051921 A2 | 4/2015 |
| WO | 2015069489 A1 | 5/2015 |
| WO | 2015171647 A1 | 11/2015 |
| WO | 2016011195 A1 | 1/2016 |
| WO | 2016011328 A2 | 1/2016 |
| WO | 2016014390 A2 | 1/2016 |
| WO | 2016081547 A1 | 5/2016 |
| WO | 2018026606 A2 | 2/2018 |
| WO | 2019055786 A2 | 3/2019 |
| WO | 2019173799 A2 | 9/2019 |
| WO | 2020007106 A1 | 1/2020 |
| WO | 2020118251 A1 | 6/2020 |

* cited by examiner

*Primary Examiner* — Timothy R Rozof

(74) *Attorney, Agent, or Firm* — Julie K. Staple; Fishman Stewart PLLC

(57) ABSTRACT

Provided in the present invention are a lyophilized formulation solution and a lyophilized formulation, and a method and the use thereof.

40 Claims, 4 Drawing Sheets

LYOPHILIZED FORMULATION SOLUTION AND LYOPHILIZED FORMULATION, AND METHOD AND USE THEREOF

CROSS-REFERENCE TO RELATED APPLICATIONS

This application claims priority to PCT International Application Serial No. PCT/C2022/115176 filed Aug. 26, 2022, which claims priority to CN Patent Application No. 202110996128.8 filed on Aug. 27, 2021, the entire content of both of which is incorporated herein by reference.

TECHNICAL FIELD

The present invention relates to the development of lyophilized formulations with TH-302 and belongs to the technical field of pharmaceutical formulations.

BACKGROUND ART

TH-302, a 2-nitroimidazole prodrug, is a selective hypoxia-activated DNA alkylating agent with high cytotoxicity that was designed and synthesized by investigators from Threshold Pharmaceuticals Inc. in 2006 (WO2007002931A2, Phosphoramidate alkylator prodrugs). It can be converted into dibromoisophosphamide chlormethine with alkylating-agent activity in hypoxic areas of tumors or upon activation with an acid, but is almost inactive under normoxic or normal pH conditions.

Investigators from Threshold Pharmaceuticals Inc. designed and developed preliminary lyophilized formulations and injection formulations in 2007 (WO2008083101A1, Phosphoramidate alkylator prodrugs for the treatment of cancer), and administered them in phase I clinical trials:

A solution (20 mL) of TH-302 (100 mg) and sucrose (1 g) was added to a lyophilized vial and lyophilized to produce a lyophilized unit dosage form of TH-302 with a drug load of less than 5 mg/cm$^3$. For purposes of human administration, the unit dosage form was dissolved in 5% dextrose injection and an appropriate amount of this solution was administered to the patient.

TH-302 was dissolved in anhydrous ethanol to produce a pharmaceutically acceptable liquid formulation containing 5% TH-302. As used herein, a solution of 5% TH-302 contains 5 g of TH-302 in 100 mL of a solvent (e.g., ethanol).

The follow-up dose regimen for the human patients in the Phase I clinical trial of TH-302 uses a lyophilized formulation. The TH-302 lyophilized formulation for injection is prepared in a 100 mL glass vial with a drug load of 100 mg/100 ml and stored under a controlled temperature of 2-8 °C. When in use, the vial containing the lyophilized formulation was injected with 250 mL of 5% dextrose and infused intravenously via an infusion pump within 30 minutes.

Investigators from Threshold Pharmaceuticals Inc. designed and developed the injection formulations in 2009 (WO2010048330A1, Treatment of cancer using hypoxia activated prodrugs):

liquid formulations, which contain 50 mg/ml to about 300 mg/ml of TH-302, nonionic surfactants (such as Tween 80), and ethanol as a carrier, and may further contain dimethylacetamide.

Clinical trials were started from 2007 and continued until now, covering a variety of solid tumors and blood cancers, and the administration regimens are also diverse: different doses of TH-302 being used alone or in combination with other cancer treatment drugs. At present, there are 27 clinical trials using TH-302 as a therapeutic drug to treat various cancers and tumors registered in the United States (NCT02402062, NCT02020226, NCT02076230, NCT01381822, NCT02093962, NCT01440088, NCT02255110, NCT02342379, NCT01864538, NCT01149915, NCT02433639, NCT00743379, NCT01485042, NCT01721941, NCT02047500, NCT00742963, NCT01497444, NCT00495144, NCT01746979, NCT01144455, NCT01403610, NCT01522872, NCT01833546, NCT02598687, NCT03098160, NCT02496832, NCT02712567). These clinical trials show that TH-302 is a broad-spectrum anti-cancer drug candidate.

After conducting the above-mentioned phase I/II clinical trials, investigators from Threshold Pharmaceuticals Inc. have found that the effective doses of TH-302 for treating various indications were as follows (WO2012135757A2, Methods for treating cancer):

a daily dose of 120 mg/m$^2$ to 460 mg/m$^2$ administered via intravenous injection; and a weekly dose of 480 mg/m$^2$ to about 670 mg/m$^2$, or, e.g., 575 mg/m$^2$, administered via intravenous injection.

According to the above effective doses, for an ordinary person (height: 175 cm, weight: 75 kg), the corresponding equivalent body surface area BSA (m$^2$)=([height (cm)×weight (kg)]/3600)$^{1/2}$=1.90, and then the corresponding dose is 228-1273 mg! In this case, if a lyophilized formulation with a drug load of less than 5 mg/cm$^3$ is used (20 mL of an aqueous solution containing 100 mg of TH-302 and 1 g of sucrose was added to a 50 ml lyophilized vial and lyophilized to produce a lyophilized unit dosage form of TH-302, and the drug load is less than 5 mg/cm$^3$), at least 3 vials are needed; and if it is used at a higher dose, 13 vials would be needed. This would be inconvenient for clinical use and also involves excessively high medication costs for patients.

For the above reasons, in most of the subsequent phase II/III clinical trials, investigators from Threshold Pharmaceuticals Inc. have used concentrated injections (WO2015013448A1, Treatment of pancreatic cancer with a combination of a hypoxia-activated prodrug and a taxane):

TH-302 (concentrate for solution for administration) for use in the trials is a sterile liquid formulation of TH-302. It is formulated with 70% anhydrous ethanol, 25% dimethylacetamide, and 5% polysorbate 80. It will be supplied by the sponsor in a 10-mL glass vial with a rubber stopper and flip-off seal. TH-302 drug product is a clear, colorless to light-yellow solution, essentially free of visible particulates. Each single use vial contains a nominal fill volume of 6.5 mL of TH-302 drug product (corresponding to 100 mg/mL) for a nominal total of 650 mg of TH-302 and will be labeled clearly. The labels disclose the lot number, route of administration, required storage conditions, sponsor's name, and appropriate precautionary labeling as required by applicable regulations. Dilution prior to administration is required per the pharmacy manual.

TH-302 drug product will be diluted prior to administration with commercially available 5% dextrose in water to a total volume of 500 mL (1000 mL for total dose of ≥1000 mg) per administration to obtain the desired final concentration. Each dose of TH-302 will be prepared with 5% dextrose aqueous solution not containing di(2-ethylhexyl) phthalate (non DEHP), and administered via intravenous drip using an intravenous infusion administration apparatus, not containing DEHP.

Apparently, it is more convenient to use concentrated injections with a drug load of 100 mg/ml in clinical trials than to use lyophilized formulations with a drug load of less than 5 mg/$cm^3$: for the former, a 10 ml gauge vial is adequate to meet the medication requirements of most patients, while for the latter, to meet the medication requirements of most patients, 13 commonly-used vials of 100 ml gauge are required!

However, investigators of Threshold Pharmaceuticals Inc. have found that the above-mentioned concentrated injection with a drug load of 100 mg/ml (i.e., the concentrated injection of TH-302 formulated with 70% anhydrous ethanol, 25% dimethylacetamide, and 5% polysorbate 80) contains a large amount of dimethylacetamide. This adjuvant that can increase drug solubility and improve the stability of injections are susceptible to cause allergies after infusion into the human body (WO2015013448A1, Treatment of pancreatic cancer with a combination of a hypoxia-activated prodrug and a taxane):

TH-302 administration reactions (which are mainly induced by dimethlyacetamide) have been observed. These reactions have been characterized by lip swelling and urticaria that responded to steroid and antihistamine treatment. It is recommended that a steroid such as dexamethasone (or equivalent) be included in the antiemetic regimen prior to administration. Symptoms and signs of hypersensitivity include fever, myalgia, headache, rash, pruritus, urticaria, angioedema, chest discomfort, dyspnea, coughing, cyanosis, and hypotension. If the nature and the severity of the reaction require termination of treatment, it should be determined whether the reaction may be an immunoglobulin E mediated process or not. If there are symptoms such as upper airway obstruction or hypotension that suggest anaphylaxis or an anaphylactoid reaction, treatment with an antihistamine (e.g., diphenhydramine 25 to 50 mg oral, intramuscular, or slow i.v., or equivalent) and a low dose of steroid (e.g., hydrocortisone, 100 mg i.v. or equivalent) should be considered by the investigators as appropriate. If the event is clearly anaphylaxis, epinephrine (1/1000, 0.3 to 0.5 mL administered subcutaneously, or equivalent) should be considered as well as standard treatment. In the case of bronchospasm, inhaled β-agonist should be considered. Idiosyncratic reactions may also be treated with an antihistamine and a low dose of steroids depending on their severity. Reactions to the administration of TH-302 should be assessed and treated in a similar manner. For all reactions to TH-302, the investigator should consult with the Medical Monitor to determine the appropriate course of action for future treatment.

High-concentration concentrated TH-302 injections have solved the problem of low drug load in lyophilized formulations. However, due to the use of the above-mentioned adjuvants that may cause adverse reactions, related adverse reactions may occur in clinical trials to result in increased risk of medication for patients.

The lyophilized formulations that have been currently developed by dissolving TH-302 with water and a sucrose solution followed by lyophilization are free of other adjuvants. However, as the drug content of the solution before lyophilization is too low, it is impossible to afford a lyophilized formulation with a high drug load that can meet the requirements for use in clinic trials and subsequent commercialized production or sales.

To solve the above-mentioned problems in reality, there remains a need to develop a lyophilized formulation of TH-302 with a high drug load and a solution for such lyophilized formulation by the technical experts in the relevant field.

SUMMARY OF THE INVENTION

After many experiments and continuous optimization, the inventors of this invention have proposed a new high-drug-concentration solution formulation for producing lyophilized formulations containing TH-302 and other similar drugs, and related lyophilized formulations and methods thereof.

In order to facilitate understanding of the essence of the present invention, the inventors' research process is briefly described below.

In order to screen suitable combinations of solvents and adjuvants to prepare a high-concentration (TH-302)

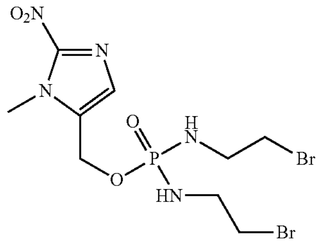

solution, the inventors initially conceived of modifying the concentrate injection with a rug load of 100 mg/ml developed by Threshold Pharmaceuticals Inc., i.e., the concentrated injection of TH-302 formulated with 70% anhydrous ethanol, 25% dimethlyacetamide, and 5% polysorbate 80:

When anhydrous ethanol and water were directly used as the solvent and sucrose was added, it was found that in some cases the resulting solutions cannot be lyophilized and only viscous oils were obtained, and in other cases, the drug contents of the solutions were limitedly increased and cannot meet the requirements. Thus, the investigators have abandoned the simple scheme of ethanol+water.

When anhydrous ethanol and water were directly used as the solvent, sucrose or other excipients were added, and the type and quantity of the solubilizers (such as PEG, Tween, and Span) to be added were adjusted, it was found that the addition of solubilizers in a small amount can increase the solubility but the increase is very limited. Thus, the requirements for high drug load cannot be met.

Considering that the pH value may affect solubility, the investigators have also studied the solubility of TH-302 in various single conventional buffer solutions. It was found that the pH value of the solution has little effect on the solubility of TH-302; and adjusting the pH value cannot improve the solubility of TH-302 in the aqueous solution. The solubility data of TH-302 in aqueous solutions at different pH values with different additives is shown in Table 1 below.

TABLE 1

| Solubility data of TH-302 in aqueous solutions at different pH values with different additives | |
|---|---|
| Different aqueous solutions | Solubility(mg/ml) |
| pH 2, HCl solution | 6.94 |
| pH 4, phthalate buffer solution | 7.22 |
| pH 6, phosphate buffer solution | 5.81 |
| pH 7, phosphate buffer solution | 5.87 |
| pH 8, phosphate buffer solution | 5.94 |
| pH 10, borate buffer solution | 6.07 |
| 1% ethanol aqueous solution | 6.58 |
| 20% ethanol aqueous solution | 8.4 |
| 1% N,N-dimethlyacetamide aqueous solution | 8.05 |
| 1% aqueous polyethylene glycol solution | 6.81 |
| 1% Tween 80 aqueous solution | 7.21 |

Note: ratios in expressions "1% ethanol aqueous solution", "20% ethanol aqueous solution", "1% N,N-dimethylacetamide aqueous solution", "1% polyethylene glycol aqueous solution", and "1% Tween 80 aqueous solution" are all volume-based ratios.

By performing numerous experiments, the inventors have confirmed that it is impossible to develop a highly-soluble solution that meets the requirements to make a TH-302 lyophilized formulation with a high drug-load via lyophilization by using merely ethanol, aqueous solutions at different pH values or ethanol+water as the solvent according to Threshold.

After many attempts, the inventors have found that TH-302 has low solubility in water or tert-butanol alone; however, they have surprisingly found that TH-302 has remarkably increased solubility in a mixed solvent of water and tert-butanol, and the solubility is highly dependent on their mixed ratios. The solubility data of TH-302 in different mixed solvents of tert-butanol+water or of tert-butanol+ethanol are shown in Table 2 below.

TABLE 2

| Solubility data of TH-302 in different mixed solvents of tert-butanol + water or of tert-butanol + ethanol | |
|---|---|
| Mixed solvents | Solubility (mg/ml) |
| tert-butanol | 8.98 |
| 95% aqueous tert-butanol solution | 32.33 |
| 90% aqueous tert-butanol solution | 76.41 |
| 80% aqueous tert-butanol solution | 88.54 |
| 40% aqueous tert-butanol solution | >40 |
| 20% aqueous tert-butanol solution | 10 |
| 95% tert-butanol/5% ethanol | 9.98 |
| 90% tert-butanol/10% ethanol | 10.72 |

Note: the ratios of mixed solvents in Table 2 refer to volume ratios, and TH-302 is purchased commercially.

Tert-butanol is a colorless crystal, easily supercooled, and becomes liquid in the presence of a small amount of water. It has a camphor-like odor and is hygroscopic. Its Chinese names include 2-methyl-2-propanol, tert-butanol, trimethylmethanol, etc. Since it has a melting point of 25.7 °C, it is a colorless transparent liquid or colorless crystal at room temperature.

Generally speaking, tert-butanol has the following characteristics:

1. High freezing point. Pure tert-butanol may crystallize at room temperature (25 °C), and can also be frozen at a few degrees below zero after being mixed with water; both pure tert-butanol and mixture of tert-butanol with water can be completely frozen in existing lyophilizers.

2. Tert-butanol has a relatively high vapor pressure. High vapor pressure is advantageous for sublimation and requires less lyophilizing time.

3. Tert-butanol is capable of being mixed with water in any ratio. This is extremely important because it enables increase of the solubility of some lipid-soluble drugs in water; and for some drugs that are unstable in aqueous solutions, adding an appropriate amount of tert-butanol can inhibit the decomposition of the drugs and enhance their stability.

4. Tert-butanol is easy to be lyophilized, and has low residual content in the formulation. During lyophilization, most of the tert-butanol may be sublimated in one drying stage, and thus its residual content in the formulation is very low.

5. Tert-butanol forms needle-like crystals during freezing, and thus can change the crystallization mode of the solute and facilitate sublimation. The tert-butanol-water co-solvent formed when a small amount of tert-butanol is added to water can change the crystallization state of water; and the needle-like crystals formed during freezing have large surface area. The sublimation of ice crystals leaves tubular channels, which allow the flow resistance for water vapor largely reduced and sublimation rate significantly increased. Accordingly, tert-butanol can be used to accelerate mass transfer during the freeze-drying processes.

In view of the above characteristics, it can be seen that tert-butanol+water as a solvent can be used for preparing a solution comprising a high-concentration compound of formula I, and tert-butanol itself is also suitable for use as an adjuvant for lyophilization owing to its intrinsic properties.

From the results of the tert-butanol-water mixed solvent shown in Table 2, it can be deduced that TH-302 has relatively low solubility in aqueous solutions; as the concentration of tert-butanol in the tert-butanol aqueous solution increases, the solubility of the active pharmaceutical ingredient increases; it is estimated that the highest solubility is reached at 70% tert-butanol aqueous solution (V/V), and then the solubility decreases as the concentration of tert-butanol in the tert-butanol aqueous solution increases.

In light of this, the inventors have proposed a scheme in which a solution with high-concentration TH-302 is obtained by using tert-butanol+water as a solvent according to the present invention and adding suitable excipient(s), and further developed lyophilized formulations with a high drug load of TH-302 or analogues thereof based on this formulation.

The inventors have further conducted experiments to investigate the effects of solvents with different volume ratio of tert-butanol on the solubility of TH-302, and the solubility data obtained are shown in Table 3 below.

TABLE 3

| Solubility data of TH-302 in tert-butanol-water mixed solvents with different tert-butanol mass ratios | |
|---|---|
| Mixed solvents | Solubility(mg/ml) |
| 100% tert-butanol | 11.77 |
| 95% tert-butanol | 36.81 |
| 90% tert-butanol | 66.60 |
| 80% tert-butanol | 143.43 |
| 75% tert-butanol | 151.23 |
| 70% tert-butanol | 164.98 |
| 60% tert-butanol | 146.33 |
| 30% tert-butanol | 41.97 |

Note: the ratios of mixed solvents in Table 3 refer to mass ratios, and TH-302 was synthesized by the applicants in small quantities.

Based on the above preliminary experiments, the present invention provides the following high-concentration solution containing TH-302 or analogs thereof.

A solution comprises a compound of the following formula I, water and tert-butanol, (I)

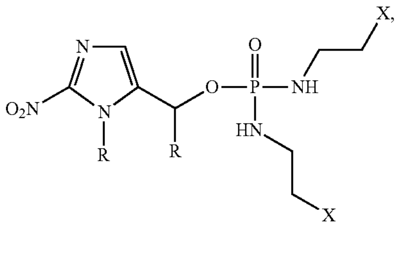

wherein R is each independently selected from H, —$CH_3$, and —$CH_2CH_3$; and X is each independently selected from Br, Cl, OMs, and OTs;

water and tert-butanol are used as a mixed solvent; and the content of the compound of formula I in the solution is greater than or equal to 1 mg/ml and less than or equal to 500 mg/ml.

Further, the present invention also provides a solution for preparing a lyophilized formulation with a high drug load, comprising a compound of the following formula I, water, tert-butanol and an excipient:

(I)

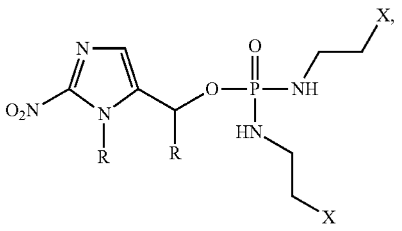

wherein R is each independently selected from H, —$CH_3$, and —$CH_2CH_3$; and X is each independently selected from Br, Cl, OMs, and OTs;

water and tert-butanol are used as a mixed solvent;

the content of the compound of formula I in the solution is greater than or equal to 5 mg/ml and less than or equal to 500 mg/ml.

preferably, the content of the compound of formula I in the solution is greater than or equal to 5 mg/ml and less than or equal to 160 mg/ml;

preferably, the content of the compound of formula I in the solution is greater than or equal to 8 mg/ml and less than or equal to 50 mg/ml;

preferably, the content of the compound of formula I in the solution is greater than or equal to 8 mg/ml and less than or equal to 25 mg/ml;

more preferably, the content of the compound of formula I in the solution is greater than or equal to 8 mg/ml and less than or equal to 15 mg/ml; and further preferably, the content of the compound of formula I in the solution is greater than or equal to 8 mg/ml and less than or equal to 10 mg/ml.

Since water and tert-butanol can be miscible in any ratio, in order to improve the solubility of TH-302 and other similar compounds, the volume percentage of tert-butanol relative to the solution is 1-99%, preferably 5-95%, and more preferably 30-60%; or the content of tert-butanol in the solution is 7.85-777.15 mg/ml, preferably 39.25-745.75 mg/ml, and more preferably 235.5-471 mg/ml.

Here, the volume percentage of tert-butanol relative to the solution being 1%-99% corresponds to the tert-butanol content of 7.85-777.15 mg/ml in the solution; specifically, when the volume percentage of tert-butanol relative to the solution is 1%, the tert-butanol content in the solution is 7.85 mg/ml. The conversion factor is the density of tert-butanol. Here, the density of tert-butanol used by the applicant is 0.785 g/ml. In actual practice, the densities of tert-butanol products from different manufacturers are different under different temperatures, generally between 0.775 and 0.786 g/ml.

The solution for preparing a lyophilized formulation with a high drug load according to the present invention comprises at least one excipient.

The term "pharmaceutically acceptable excipient" refers to any additive or carrier that may contribute to the stability of active pharmaceutical ingredients in the formulation. During the preparation process of the lyophilized formulation, it is essential to add an excipient or a lyo-protectant to a solution used for lyophilization.

Some drug solutions can be successfully freeze-dried in vacuum, while others would quickly collapse or be melt into oily substances after lyophilization. In order to obtain stable lyophilized formulations by successfully lyophilizing certain drug solutions, some excipients that do not react with the drugs need to be added. Such excipients per se will not be sublimated in the sublimation stage of the lyophilizing process; instead, they can be directly lyophilized into skeletons and thus play a role of giving form; the drugs can be directly adsorbed on or filled in the gaps of the skeletons; or they can improve the solubility and stability of the lyophilized products, or they can enable the lyophilized products to have an aesthetical shape, etc. It is required to add some additional substances into the liquid formulations. The additional substances are collectively called "lyo-protectants", and sometimes they are also called fillers, bulking agents, excipients, buffers, base materials, skeletons, etc. In general, lyo-protectants must be chemically inert to the drug solution.

Depending on their chemistry, lyo-protectants can be classified into the following categories:

Compounds: skim milk, gelatins, proteins and hydrolyzates thereof, peptides, yeasts, broths, dextrins, methylcellulose, serum, peptone, etc.;

Salts: sodium thiosulfate, calcium lactate, sodium glutamate, sodium chloride, potassium chloride, sodium sulfate, ammonium acetate, ammonium chloride, etc.;

Saccharides: sucrose, lactose, maltose, glucose, raffinose, fructose, hexose, etc.;

Alcohols: sorbitol, ethanol, glycerin, mannitol, inositol, xylitol, etc.;

Acids: citric acid, phosphoric acid, tartaric acid, amino acids, ethylenediaminetetraacetic acid (EDTA), etc.;

Bases: sodium hydroxide, sodium bicarbonate, etc.;

Polymers: dextran, polyethylene glycol, polysorbate, PVP, poloxamer, etc.; and

Others: vitamin C, vitamin E, vitamin K, thiourea, etc.

The degree of polymerization (molecular weight) of the above-mentioned polymers is in a broad range. Polysorbates and polyethylene glycols are cited as the examples.

Polysorbate may have an average molecular weight ranging from about 500 g/mol to about 1900 g/mol, preferably from about 800 g/mol to about 1600 g/mol, and more preferably from about 1000 g/mol to about 1400 g/mol. Non-limiting examples of polysorbates include: polysorbate-20, polysorbate-21, polysorbate-40, polysorbate-60, polysorbate-61, polysorbate-65, polysorbate-81, polysorbate-85 and polysorbate-120. Preferred polysorbates include polysorbate-20, polysorbate-80, and a mixture thereof.

Polyethylene glycols (PEGs) may have an average molecular weight ranging from about 200 g/mol to about 600 g/mol, preferably from about 200 g/mol to about 500 g/mol, and more preferably from about 200 g/mol to about 400 g/mol. Non-limiting examples of PEGs include: PEG200, PEG300, PEG400, PEG540 and PEG600.

Poloxamer has a general formula of $HO(C_2H_4O)_n(C_3H_6O)_b(C_2H_4O)_cH$, wherein a and c are in the range of 2-130 and b is in the range of 15-67. It contains 81.8±1.9% of polyoxyethylene and is a polyoxyethylene polyoxypropylene ether block copolymer. It has different brands: poloxamer 182, poloxamer 184, poloxamer 188, and poloxamer 407, which correspond to polymers with different molecular weights, such as Poloxamer 188 having a molecular weight of 7680-9510.

The lyo-protectant serves many functions, which are specifically summarized as follows.

Microorganisms such as bacteria and viruses need to grow and reproduce in particular culture media. However, the microorganisms are difficult to be separated from the culture media and thus may be successfully lyophilized in these culture media. Examples of culture media are broth, skim milk and protein, etc.

Some lyophilized formulations have very low concentration and minor dry matter content. During lyophilization, the dried components will be taken away by the sublimation airflow. In order to increase the drug concentration and the dry matter content to enable the lyophilized products to form relatively ideal agglomerates, it is necessary to add fillers to keep the concentration of the solid matter within a certain range. These fillers or excipients include sucrose, lactose, inositol, skim milk, hydrolyzed protein, dextran, sorbitol, polyvinylpyrrolidone (PVP), etc.

Some biologically active substances are particularly fragile and may be injured owing to physical or chemical factors during freezing and drying. Therefore, some protective agents (for example, dimethyl sulfoxide, glycerol, dextran, saccharides and PVP) need to be added to reduce damage during freezing and drying.

Adding certain substances (e.g., mannitol, glycine, dextran, xylitol and PVP) can increase the disintegration temperature of the product and make it easy to be lyophilized.

In order to change the pH of the lyophilized formulation to increase the eutectic point to facilitate lyophilization, sodium bicarbonate, sodium hydroxide, or the like may be added.

For the purpose of improving the storage stability of the product, increasing the storage temperature and prolonging the storage period, some antioxidants such as vitamin C, vitamin E, amino acids, sodium thiosulfate, thiourea, lecithin and hydrolyzed protein may be added.

Adding certain substances (e.g., amino acids, vitamin K, vitamin C, thiourea, sulfite compounds, and sodium aspartate) can eliminate free radicals and increase the stability of the lyophilized product.

It can be found that a single compound can play multiple roles as a lyo-protectant (excipient).

According to the properties of the drug of the present invention, the lyo-protectant (excipient) is selected from saccharides, polyols, polyvinylpyrrolidones, proteins, poloxamer or a combination thereof.

The saccharide is selected from sucrose, dextran, cyclodextrin, maltodextrin, trehalose, lactose, maltose, and glucose.

The polyol is selected from the group consisting of glycerin, sorbitol, mannitol, inositol, ethylene glycol, polyethylene glycol (PEG), polysorbate, and adonitol.

The protein is selected from albumin, preferably bovine serum albumin and human albumin.

The poloxamer is selected from poloxamer 182, poloxamer 184, poloxamer 188, and poloxamer 407.

Preferably, the excipient is selected from PVP K12, sucrose, mannitol, albumin or a combination thereof.

Generally speaking, excipients of the same type can be combined, and the excipients that do not react with each other and with drugs can be combined. The combination should meet the drug compatibility requirements.

In particular, the excipient is selected from sucrose and mannitol; and the content of sucrose or mannitol in the solution is in the range of 20-300 mg/ml, preferably in the range of 40-100 mg/ml, more preferably in the range of 60-80 mg/ml, and further preferably in the range of 60-70 mg/ml.

Generally only one of sucrose and mannitol is used, but in some special cases, sucrose and mannitol can also be mixed used. In the preferred embodiments of the present invention, only mannitol or sucrose is used.

Analogously, the mass ratio of TH-302 in the solution for preparing the lyophilized formulation with a high drug load to the excipient(s) is in the range of 1: (0.5-20), preferably in the range of 1: (1-15), more preferably in the range of 1: (2-12.5), and further preferably in the range of 1:(5-10).

The mass ratio of TH-302 and other similar compounds to the excipient is the drug loading ratio of the solution for lyophilization. According to the lyophilized state of the above-mentioned excipients (lyo-protectants, fillers, or skeletons), it can be seen that the lyophilized body after lyophilization has skeletons obtained from the excipient(s), and the drug(s) will be adsorbed on or loaded onto the skeletons. Thus, the drug loading ratio of the drug solution prior to lyophilization, i.e., mass ratio of TH-302 to the excipient(s), is an important index.

Appropriate drug loading ratio means that after lyophilization of the lyophilized formulation, the drug is evenly adsorbed on the skeletons, and the drug will be well distributed in the gaps and pore surfaces of the skeletons; thus, during subsequent reconstitution (with 5% dextrose injection, physiological saline, etc.), the lyophilized formulation can be rapidly and well dissolved to be ready for injection administration.

"Pharmaceutically acceptable buffer" refers to weak acids or bases that allow the pH value of the solution to be maintained at an almost constant level and are used to enhance the stability of the active pharmaceutical ingredient in the solution.

The solution for preparing the lyophilized formulation with high drug load according to the present invention can also comprise at least one buffer, and the buffer is selected from the group consisting of citrate buffer, borate buffer, lithium lactate, sodium lactate, potassium lactate, calcium lactate, lithium phosphate, sodium phosphate, potassium phosphate, calcium phosphate, lithium maleate, sodium maleate, potassium maleate, calcium maleate, lithium tartrate, sodium tartrate, potassium tartrate, calcium tartrate, lithium succinate, sodium succinate, potassium succinate, calcium succinate, lithium acetate, sodium acetate, potassium acetate, calcium acetate, or a mixture thereof.

Preferably, the buffer used in the solution for preparing the lyophilized formulation with high drug load according to the present invention is at least one citrate buffer. Non-limiting examples of suitable citrate buffers include: lithium citrate monohydrate, sodium citrate monohydrate, potassium citrate monohydrate, calcium citrate monohydrate, lithium citrate dihydrate, sodium citrate dihydrate, potassium citrate dihydrate, calcium citrate dihydrate, lithium citrate trihydrate, sodium citrate trihydrate, potassium citrate trihydrate, calcium citrate trihydrate, lithium citrate tetrahydrate, sodium citrate tetrahydrate, potassium citrate tetrahydrate, calcium citrate tetrahydrate, lithium citrate pentahydrate, sodium citrate pentahydrate, potassium citrate pentahydrate, calcium citrate pentahydrate, lithium citrate hexahydrate, sodium citrate hexahydrate, potassium citrate hexahydrate, calcium citrate hexahydrate, lithium citrate heptahydrate, sodium citrate heptahydrate, potassium citrate heptahydrate, and calcium citrate heptahydrate.

The solution for preparing the lyophilized formulation with a high drug load according to the present invention can also comprise at least one pH regulator.

The pH regulator of the present invention refers to a buffer substance or buffer solution used to appropriately adjust the pH changing with acid or alkali. The pH regulator includes, but is not limited to, hydrochloric acid, sodium hydroxide, triethanolamine, phosphoric acid, disodium hydrogen phosphate, dipotassium hydrogen phosphate, sodium dihydrogen phosphate, potassium dihydrogen phosphate; or phosphoric acid, citric acid, lactic acid, tartaric acid, succinic acid, fumaric acid, malic acid, sodium bicarbonate, sodium carbonate or a mixture thereof. The content of the pH regulator to be added is such that the pH value of the solution is in the range of 4-9, preferably in the range of 6-8.

Since TH-302 and its analogs are usually acidic (the preparation process of the compound involves an acidic environment and slight hydrolysis, the active pharmaceutical ingredient prepared or purchased will be acidic), the pH regulator is preferably selected from a base such as sodium hydroxide, triethanolamine, sodium bicarbonate, and sodium carbonate, or an alkaline salt.

Of course, it is also possible that the pH of TH-302 and its analogs is alkaline due to other factors. In this case, an acid or acidic salt (such as ammonium sulfate and ammonium chloride) needs to be added for adjusting the pH.

The compound of the following formula I is selected from (TH-302 or I-1)

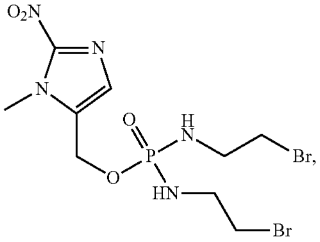

-continued (I-2)

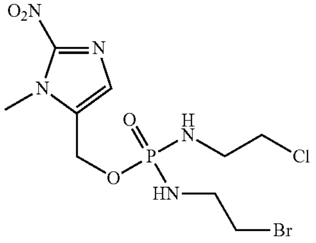

or (I-3)

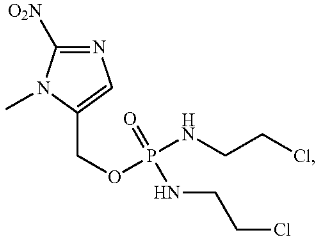

and more preferably TH-302.

The specific synthesis method of the compound of formula I and the corresponding spectral data are disclosed in WO2007002931 (corresponding to Chinese publication CN101501054A), which is incorporated herein by reference in its entirety.

For the relevant physiochemical properties and biological activities of the compound of formula I and the three specific compounds, please refer to the patents owned by Threshold Pharmaceuticals Inc. (such as WO2016011195A2, WO2004087075A1, WO2007002931A1, WO2008151253A2, WO2009018163A1, WO2009033165A2, WO2010048330 A2, WO2012142520A1, WO2008083101A2, WO2020007106A1, WO2020118251A1, WO2014169035A1, WO2013116385A1, WO2019173799A2, WO2016081547A1, WO2014062856A1, WO2015069489A1, WO2012006032A2, WO2018026606A2, WO2010048330A2, WO2015171647A1, WO2013096687A1, WO2013126539A2, WO2013096684A2, WO2012009288A2, WO2012145684A2, WO2016014390A2, WO2019055786A2, WO2012135757A2, WO2015013448A2, WO2016011328A2, WO2013177633A2, WO2016011195A2, and WO2015051921A2), which are incorporated herein by reference in their entirety.

The three preferred compounds have the same or similar physiochemical properties to TH-302.

The present invention provides a solution for preparing a lyophilized formulation with a high drug load, comprising

- a compound of the following formula I-1, water, tert-butanol and sucrose; or
- a compound of the following formula I-1, water, tert-butanol and mannitol;

(I-1)

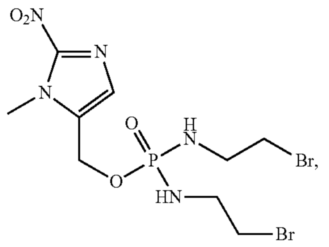

water and tert-butanol are used as a mixed solvent;

the volume content of tert-butanol relative to the solution is 30%, 40%, or 60%, or the content of tert-butanol in the solution is 235.5, 314, or 471 mg/ml;

the content of the compound of formula I-1 in the solution is 6, 7, 7.5, 8, 8.5, 10, 12.5, 15, 20, or 25 mg/ml;

sucrose or mannitol is used as an excipient, and the content of sucrose or mannitol in the solution is 40, 50, 60, 70, 75, 80, 90, or 100 mg/ml.

The present invention provides a solution for preparing a lyophilized formulation with a high drug load, comprising a compound of the following formula I-1, water, tert-butanol, sucrose and a pH regulator, or a compound of the following formula I-1, water, tert-butanol, mannitol, and a pH regulator, (I-1)

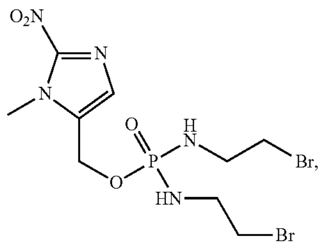

water and tert-butanol are used as a mixed solvent;

the volume content of tert-butanol relative to the solution is 30%, 40%, or 60%, or the content of tert-butanol in the solution is 235.5, 314, or 471 mg/ml;

the content of the compound of formula I-1 in the solution is 6, 7, 7.5, 8, 8.5, 10, 12.5, 15, 20, or 25 mg/ml;

sucrose or mannitol is used as an excipient, and the content of sucrose or mannitol in the solution is 40, 50, 60, 70, 75, 80, 90, or 100 mg/ml, the content of the pH regulator is such that the pH value of the solution is in the range of 4-9, preferably in the range of 6-8.

The present invention provides a solution for preparing a lyophilized formulation with a high drug load, consisting of a compound of the following formula I-1, water, tert-butanol, sucrose, and sodium bicarbonate; or a compound of the following formula I-1, water, tert-butanol, mannitol, and sodium bicarbonate;

(I-1)

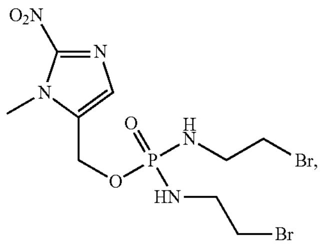

water and tert-butanol are used as a mixed solvent;

the volume content of tert-butanol relative to the solution is 30%, 40%, or 60%, or the content of tert-butanol in the solution is 235.5, 314, or 471 mg/ml;

the content of the compound of formula I-1 in the solution is 6, 7, 7.5, 8, 8.5, 10, 12.5, 15, 20, or 25 mg/ml;

sucrose or mannitol is used as an excipient, and the content of sucrose or mannitol in the solution is 40, 50, 60, 70, 75, 80, 90, or 100 mg/ml; and the content of the sodium bicarbonate is such that the pH value of the solution is in the range of 4-9, and preferably in the range of 6-8.

In the above-mentioned solution for preparing a lyophilized formulation with a high drug load, wherein the mass ratio of the compound to sucrose or mannitol is 1:2, 1:3, 1:3.5, 1:4, 1:5, 1:5.333, 1:5.6, 1:6, 1:1.67, 1:7, 1:8, 1:8.235, 1:8.75, or 1:9.375.

Of course, buffers, pH regulators or other auxiliary materials for the lyophilized formulations can also be added according to the above illustrations and depending on the properties of the specific compound of formula I.

Apparently, if other substances (environmental substances) are detected due to contact with or contamination of containers, pipes, and tools during the preparation of the solution, they do not belong to the category of such auxiliary materials. Similarly, tert-butanol, sucrose/mannitol, and the raw materials of the compound of formula I are inevitably doped with impurities or other substances involved in the environment (environmental substances). These impurities or environmental substances are also not included in said category of auxiliary materials.

The contents of all the other substances (environmental substances) detected due to contact with or contamination of containers, pipes, and tools and the impurities or the other substances involved in the environment (environmental substances) inevitably doped in tert-butanol, sucrose/mannitol, and the raw materials of the compound of formula I should be within the statutory limits or comply with quality standards (pharmaceutical grade, medical grade or equivalent quality standards) of the corresponding products.

Apparently, if other substances (environmental substances) are detected due to contact with or contamination of containers, pipes, and tools during the preparation of the solution, they do not belong to the category of such auxiliary materials. Similarly, tert-butanol, sucrose/mannitol, sodium bicarbonate and the raw materials of the compound of formula I are inevitably doped with impurities or other substances involved in the environment (environmental substances). These impurities or environmental substances are also not included in said category of auxiliary materials.

The contents of all the other substances (environmental substances) detected due to contact with or contamination of containers, pipes, and tools, and the impurities or the other substances involved in the environment (environmental substances) inevitably doped in tert-butanol, sucrose/mannitol, and the raw materials of the compound of formula I, should be within the statutory limits or comply with quality standards (pharmaceutical grade, medical grade or equivalent quality standards) of the corresponding products.

Therefore, the above-mentioned expression "consisting of . . . " refers to substances that are intentionally or artificially added during preparation (these substances are essential to be contained and can be detected by analytical testing instruments). In addition to these substances, there are no other intentionally or artificially added substances. However, there will still be inevitablely trace amounts of impurities, environmental substances, or the like.

The above contents explain the constituents (formulation) of the solution for preparing the lyophilized formulation with a high drug load, and its use is briefly described below.

The solution provided above is only used as an intermediate semi-finished product for preparing the lyophilized formulation with a high drug load and cannot be used for clinical formulations. Generally speaking, it is readily prepared for use at the production site; that is, it is prepared in a liquid-formulating container and directly filled into lyophilized vials, and then sent into the lyophilizing production equipment in batches for lyophilization.

Therefore, it should be ensured that the solution for preparing the lyophilized formulation with a high drug load is stable after preparation and during production and waiting process for being lyophilized in the lyophilizing equipment, it should be stable at room temperature for at least 8 hours, and preferably for 24 hours or even 72 hours, or for 120 hours.

This is because the solution needs to be filtered and filled before it is sent into a lyophilizer for lyophilization after preparation. Filtration and filling are usually completed within 8-12 hours and are generally performed at room temperature. Despite this, the subsequent lyophilization is conducted at low temperature and it takes 20-60 hours for a large-scale lyophilizer or lyophilizing system to cool the large amount of drug liquid filled in vials to the set low temperature (−20 °C to −55 °C). Thus, the drug solution for the lyophilized formulation should be stable within a certain period of time and at room temperature. After experiments, the inventors have validated that the drug solution for the lyophilized formulation of TH-302 provided by the present invention has appropriate stability.

The present invention also provides use of a solution for preparing the lyophilized formulation with a high drug-load. The solution is suitable for use as a lyophilized formulation solution and is used for preparation of the lyophilized formulation by a lyophilization process.

Based on the above-mentioned solution for preparing the lyophilized formulation with a high drug-load, the present invention can provide lyophilized formulations with a high drug-load.

A lyophilized formulation is prepared using the above-mentioned solution for preparing a lyophilized formulation with a high drug-load as a lyophilized formulation solution by a lyophilization process.

A lyophilized formulation comprises a compound of the following formula I, an excipient and residual solvent components,

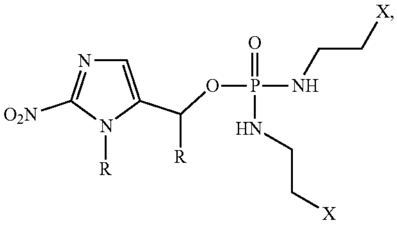

(I)

wherein R is each independently selected from H, $—CH_3$, and $—CH_2CH_3$; and X is each independently selected from Br, Cl, OMs, and OTs;

the drug load of the compound of formula I in the lyophilized formulation is greater than 5 mg/$cm^3$ and less than or equal to 555.55 mg/$cm^3$, or the drug load of the compound of formula I in the lyophilized formulation is greater than or equal to 4.55 mg/$cm^3$ and less than 500 mg/$cm^3$, or the mass percentage of the compound of formula I in the lyophilized formulation is greater than or equal to 4.39% and less than 66.66%, and the residual solvent components are water and tert-butanol.

A lyophilized formulation comprises a compound of the following formula I, an excipient, residual solvent components and a pH regulator,

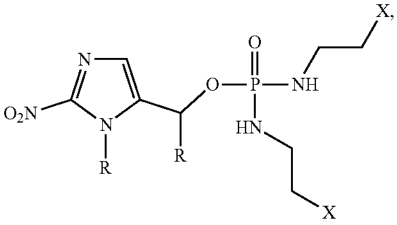

(I)

wherein R is each independently selected from H, $—CH_3$, and $—CH_2CH_3$; and X is each independently selected from Br, Cl, OMs, and OTs;

the drug load of the compound of formula I in the lyophilized formulation is greater than 5 mg/$cm^3$ and less than or equal to 555.55 mg/$cm^3$, or the drug load of the compound of formula I in the lyophilized formulation is greater than or equal to 4.55 mg/$cm^3$ and less than 500 mg/$cm^3$, or the mass percentage of the compound of formula I in the lyophilized formulation is greater than or equal to 4.39% and less than 66.66%, and the residual solvent components are water and tert-butanol.

A lyophilized formulation comprises a compound of the following formula I and an excipient,

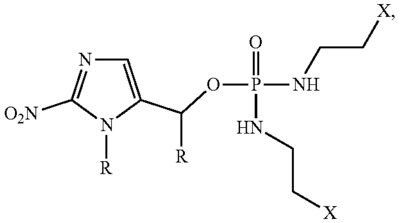

(I)

wherein R is each independently selected from H, $—CH_3$, and $—CH_2CH_3$; and X is each independently selected from Br, Cl, OMs, and OTs;

the drug load of the compound of formula I in the lyophilized formulation is greater than 5 mg/cm$^3$ and less than or equal to 555.55 mg/cm$^3$, or the drug load of the compound of formula I in the lyophilized formulation is greater than or equal to 4.55 mg/cm$^3$ and less than 500 mg/cm$^3$, or the mass percentage of the compound of formula I in the lyophilized formulation is greater than or equal to 4.39% and less than 66.66%.

Here, the drug load of the compound of formula I in the lyophilized formulation being greater than 5 mg/cm$^3$ and less than or equal to 555.55 mg/cm$^3$, and the drug load of the compound of formula I in the lyophilized formulation being greater than or equal to 4.55 mg/cm$^3$ and less than 500 mg/cm$^3$ denote two different situations.

After extensive experiments, the applicants have found that in the case of using 50 ml vial and a maximum filling volume of 25 ml, for different lyophilized processes of lyophilizing the above-mentioned lyophilized formulation solution with a high drug load to afford a lyophilized formulation, there is a change of less than 10% between the volume of the pre-lyophilization solution and the external volume of the lyophilized formulation solid; the volume may be increased by 10% due to expansion of the lyophilized cake after lyophilization, or it may be reduced by 10% due to collapse of the powder cake. It is calculated based on the content of the compound of formula I in the lyophilized formulation solution with a high drug load before lyophilization being greater than or equal to 5 mg/ml and less than or equal to 500 mg/ml and the maximum change of 10% that, the volume is 1.1 times that of the original volume due to the expansion, or is 90% of the original volume due to the collapse. Taking the volume of the collapsed powder cake after lyophilization being 90% of the original volume as an example, the maximum drug load of the powder cake here is calculated to be 5/0.9=5.55 to 500/0.9=555.55. Depending on the process, there may be a situation where the volume does not change. In this case, the drug load is ranging from 5 to 500. The two ranges are combined to be 5 to 555.55; that is, the drug load of the compound of formula I in the lyophilized formulation is greater than 5 mg/cm$^3$ and less than or equal to 555.55 mg/cm$^3$.

Analogously, when the volume is increased due to the expansion of the lyophilized cake, the drug load of the compound of formula I in the lyophilized formulation is greater than or equal to 4.55 mg/cm$^3$ and less than 500 mg/cm$^3$.

The drug load of the lyophilized formulation provided by the present invention refers to the amount of the compound of formula I as the active pharmaceutical ingredient contained per unit volume; and the volume here refers to the total external volume of the drug in the unit packaging kit, including the internal voids of the drug. For example, a 20 ml of the lyophilized solution in a 100 ml lyophilized vial contains 500 mg of the drug. After the pre-lyophilization solution has been lyophilized, the 20 ml of the solution will be frozen into a loose and porous lyophilized formulation. When the bottom area of the inner space of the lyophilized vial is measured as s, and the height of the lyophilized formulation in the lyophilized vial as h, then the total external volume of this unit-packaged lyophilized formulation is sh; since 500 mg of the active pharmaceutical ingredient is loaded, its drug load is (500/sh) mg/cm$^3$. Generally, the value of sh will be about 20 cm$^3$. The volume after lyophilization may be greater than 20 cm$^3$ due to the expansion, or the volume after lyophilization may be less than 20 cm$^3$ due to the collapse.

When the drug load of the lyophilized formulation packaged in a certain unit package is determined, the total external volume sh mentioned above is initially measured and calculated, and then all the lyophilized formulation packaged in the unit package is directly dissolved and the mass M of the drug contained therein is measured; and thus the drug load (per unit volume) of the lyophilized formulation of the present invention=M/sh.

Here, the mass percentage of the compound of formula I in the lyophilized formulation is greater than or equal to 40.39% and less than 66.66%. It can be converted based on the API content, and contents of excipients, and residual tert-butanol and water in the lyophilized formulation.

The mass content of the compound of formula I in a lyophilized formulation refers to the percentage of the drug relative to the total mass of the lyophilized formulation. It can be measured and calculated according to the following operations:

When measuring the drug mass content of the lyophilized formulation packaged in a certain unit package, the mass M1 of the lyophilized formulation in the unit package is initially weighed, and then the all the lyophilized formulations in the unit package is directly dissolved and the mass M of the drug contained therein is measured. When a total mass of the empty vial and packaging cap that have been cleaned, oven dried and weighed after dissolution is taken as M2, the total mass of the lyophilized formulation is M1-M2, then the mass content of the compound of formula I in the lyophilized formulation according to the present invention=M/(M1-M2).

In the above-mentioned lyophilized formulation, the compound of formula I is selected from (TH-302)

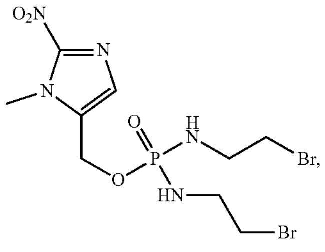

-continued

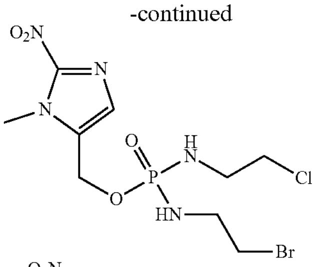

or

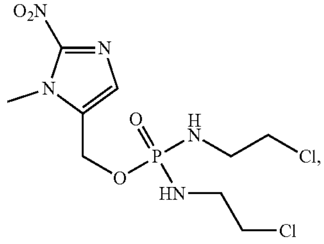

, preferably TH-302.

The excipient is selected from saccharides, polyols, polyvinylpyrrolidones, proteins, poloxamer or a combination thereof;

- the saccharide is selected from sucrose, dextran, cyclodextrin, maltodextrin, trehalose, lactose, maltose, and glucose;
- the polyol is selected from the group consisting of glycerin, sorbitol, mannitol, inositol, ethylene glycol, polyethylene glycol, polysorbate, and adonitol;
- the protein is selected from albumin, preferably bovine serum albumin and human albumin; and
- the poloxamer is selected from poloxamer 182, poloxamer 184, poloxamer 188, and poloxamer 407.

After the solution has been lyophilized, water and tert-butanol as the solvent will be sublimated.

Thus, the lyophilized formulation only contains the remaining drug and excipients.

Apparently, since it is impossible to completely remove water and tert-butanol during the sublimation process of lyophilization, the residues of water and tert-butanol are inevitably included. In fact, the residual amount of water and tert-butanol is an important quality index for the lyophilized formulation: the lower the residual amount, the better the quality and stability of the lyophilized formulation will be, and after administration with such a formulation, a patient will experience less adverse reactions. Minimizing the residual amount can be fulfilled by adjusting the lyophilization process. However, residues cannot be completely avoided.

Nonetheless, by prolonging the lyophilization time and elevating the drying temperature, it is technically feasible to reduce the content of water and tert-butanol to be lower than the detection limit regardless of costs while complying with the product quality requirements. In this case, the lyophilized formulation can be considered as being almost free of water and tert-butanol.

Considering the production cost and storage stability, there are appropriate residual contents for water and tert-butanol respectively as follows: the residual water content is less than or equal to 6% by mass, preferably less than or equal to 2%, more preferably less than or equal to 1%, and further preferably less than or equal to 0.5%; and the residual tert-butanol content is less than or equal to 1.75% by mass, preferably less than or equal to 1%, and more preferably less than or equal to 0.5%.

Of course, buffers, pH regulators or other auxiliary materials for the lyophilized formulations can also be added according to the above illustrations and in combination with the properties of the specific compound of formula I. Correspondingly, the lyophilized formulations will also be detected to contain buffers, pH regulators or other adjuvants for lyophilization.

Apparently, if other substances (environmental substances), which cannot be removed by sublimation, are detected due to contact with or contamination of containers, pipes, and tools, they do not belong to the category of such auxiliary materials. Similarly, tert-butanol, sucrose, and raw materials of the compound of formula I are inevitably doped with impurities or other substances involved in the environment (environmental substances) that cannot be removed by sublimation. These impurities or environmental substances are also not included in said category of auxiliary materials.

The contents of all the other substances (environmental substances) that cannot be removed by sublimation and are detected due to contact with or contamination of containers, pipes, and tools, and impurities or other substances involved in the environment (environmental substances) that cannot be removed by sublimation inevitably doped in tert-butanol, sucrose/mannitol, and the raw materials of the compound of formula I should be within the statutory limits or comply with quality standards (pharmaceutical grade, medical grade or equivalent quality standards) of the corresponding products.

"Comprising/comprise the compound of the following formula I and excipients" means that in addition to the inevitable, residual water and tert-butanol, the lyophilized formulation can be detected to contain the compound of formula I, excipients and the above-mentioned residual environmental substances. In addition, it can also contain other adjuvants.

The mass ratio of the compound of formula I to the excipient is in the range of 1: (0.5-20), preferably in the range of 1: (1-15), more preferably in the range of 1: (2-12.5), and further preferably in the range of 1:(5-10).

The drug load of the compound of formula I in the lyophilized formulation is greater than or equal to 5.55 mg/cm$^3$ and less than or equal to 177.77 mg/cm$^3$, preferably greater than or equal to 8.88 mg/cm$^3$ and less than or equal to 55.55 mg/cm$^3$, more preferably greater than or equal to 8.88 mg/cm$^3$ and less than or equal to 27.77 mg/cm$^3$, more preferably greater than or equal to 8.88 mg/cm$^3$ and less than or equal to 16.66 mg/cm$^3$, and further more preferably greater than or equal to 8.88 mg/cm$^3$ and less than or equal to 11.11 mg/cm$^3$; or the drug load of the compound of formula I in the lyophilized formulation is greater than or equal to 4.55 mg/cm$^3$ and less than or equal to 145.45 mg/cm$^3$, preferably greater than or equal to 7.27 mg/cm$^3$ and less than or equal to 45.45 mg/cm$^3$, more preferably greater than or equal to 7.27 mg/cm$^3$ and less than or equal to 22.73 mg/cm$^3$, more preferably greater than or equal to 7.27 mg/cm$^3$ and less than or equal to 13.64 mg/cm$^3$, and further more preferably greater than or equal to 7.27 mg/cm$^3$ and less than or equal to 9.09 mg/cm$^3$.

For the above two situations mentioned here, the former refers to the situation where the volume becomes smaller after lyophilization due to the collapse, and the latter is the situation where the volume becomes larger due to the expansion.

A lyophilized formulation is essentially consisting of the compound of the following formula I-1, an excipient, residual water and residual tert-butanol, (I-1)

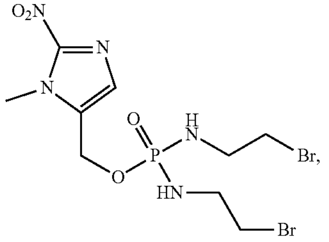

wherein the drug load of the compound in the lyophilized formulation is 6.66, 7.77, 8.33, 8.88, 9.44, 11.11, 13.88, 16.66, 22.22, or 27.77 mg/cm$^3$, or the drug load of the compound in the lyophilized formulation is 5.45, 6.36, 6.82, 7.27, 7.73, 9.09, 11.36, 13.64, 18.18, or 22.73 mg/cm$^3$;

the excipient is sucrose or mannitol;

the mass ratio of the compound to the excipient is 1:2, 1:3, 1:3.5, 1:4, 1:5, 1:5.333, 1:5.6, 1:6, 1:7, 1:8, 1:8.235, 1:8.75, or 1:9.375;

the residual water content is less than or equal to 6% by mass, preferably less than or equal to 2% by mass, more preferably less than or equal to 1% by mass, and further preferably less than or equal to 0.5% by mass; and the residual tert-butanol content is less than or equal to 1.75% by mass, preferably less than or equal to 1% by mass, and more preferably less than or equal to 0.5% by mass.

A lyophilized formulation is essentially consisting of the compound of the following formula I-1, an excipient, residual water, residual tert-butanol and a pH regulator, (I-1)

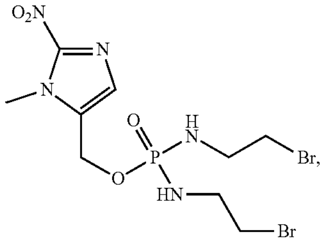

wherein the drug load of the compound in the lyophilized formulation is 6.66, 7.77, 8.33, 8.88, 9.44, 11.11, 13.88, 16.66, 22.22, or 27.77 mg/cm$^3$, or the drug load of the compound I-1 in the lyophilized formulation is 5.45, 6.36, 6.82, 7.27, 7.73, 9.09, 11.36, 13.64, 18.18, or 22.73 mg/cm$^3$;

the excipient is sucrose or mannitol;

the mass ratio of the compound to the excipient is 1:2, 1:3, 1:3.5, 1:4, 1:5, 1:5.333, 1:5.6, 1:6, 1:1.67, 1:7, 1:8, 1:8.235, 1:8.75, or 1:9.375.

the residual water content is less than or equal to 6% by mass, preferably less than or equal to 2% by mass, more preferably less than or equal to 1% by mass, and further preferably less than or equal to 0.5% by mass;

the residual tert-butanol content is less than or equal to 1.75% by mass, preferably less than or equal to 1% by mass, and more preferably less than or equal to 0.5% by mass; and the pH regulator is sodium bicarbonate, which is present in an amount of 0.01-0.10 mg/cm$^3$.

A lyophilized formulation is essentially consisting of the compound of the following formula and an excipient, (I-1)

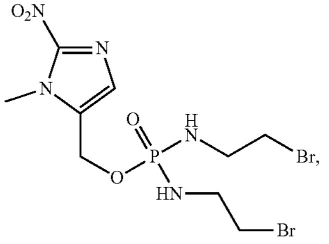

wherein the drug load of the compound of formula I-1 is 6.66, 7.77, 8.33, 8.88, 9.44, 11.11, 13.88, 16.66, 22.22, or 27.77 mg/cm$^3$, or the drug load of the compound of formula I-1 is 5.45, 6.36, 6.82, 7.27, 7.73, 9.09, 11.36, 13.64, 18.18, or 22.73 mg/cm$^3$;

the excipient is sucrose or mannitol;

the mass ratio of the compound of formula I-1 to the excipient is 1:2, 1:3, 1:3.5, 1:4, 1:5, 1:5.333, 1:5.6, 1:6, 1:1.67, 1:7, 1:8, 1:8.235, 1:8.75, or 1:9.375.

Apparently, if other substances (environmental substances), which cannot be removed by sublimation are detected due to contact with or contamination of containers, pipes, and tools during the preparation of the solution, they do not belong to the category of such auxiliary materials. Similarly, tert-butanol, sucrose, and raw materials of the compound of formula I are inevitably doped with impurities or other substances involved in the environment (environmental substances) that cannot be removed by sublimation. These impurities or environmental substances are also not included in said category of auxiliary materials.

The contents of all the other substances (environmental substances), which cannot be removed by sublimation and are detected due to contact with or contamination of containers, pipes, and tools, and the impurities or other substances involved in the environment (environmental substances) that cannot be removed by sublimation inevitably doped in tert-butanol, sucrose/mannitol, and the raw materials of the compound of formula I should be within the statutory limits or comply with quality standards (pharmaceutical grade, medical grade or equivalent quality standards) of the corresponding products.

"Comprising/comprise the compound of the following formula I and excipients" means that in addition to the inevitable, residual water and tert-butanol, the lyophilized formulation can be detected to contain the compound of formula I, excipients and the above-mentioned residual environmental substances. In addition, it can also contain other adjuvants.

"Essentially consisting of the compound of the following formula I and excipients" means that in addition to the inevitable, residual water and tert-butanol, the lyophilized formulation can be detected to only contain the compound of formula I, excipients and the above-mentioned residual environmental substances. Apart from such components, it is free of other substances.

The present invention provides a lyophilized formulation, which is prepared through a lyophilization process by using the above-mentioned solutions for preparing a lyophilized formulation with a high drug load.

The pharmaceutical formulation and the lyophilized powders thereof can be stored in containers commonly used in the pharmaceutical field, which may include: plastic containers or glass containers, such as standard USPI type borosilicate glass containers. For example, the container to be used may be a syringe or a vial.

According to the dosages of the compound of formula I used in the animal model experiments and clinical trials described in the background art portion of this application, it can be known that the dosage of the compound to be administered each time may vary when used in different species (human beings and other animals), or against different indications, or in different patients, and it may range from the minimal amount of a few milligrams to the maximum amount of tens of thousands of milligrams. It is most preferable that a unit dose package or a combination of multiple unit dose packages can meet the dosage for a certain administration. Therefore, in view of the above, we have given recommendations for suitable dosages of the lyophilized formulation per unit package for different species or against different indications.

The present invention also provides a formulation unit package containing said lyophilized formulation:

- the lyophilized formulation is contained in a sealed container with a capacity of 1000 ml; the volume of the lyophilized formulation is ⅕ to ⅔, preferably ⅓ to ½ of the volume of the sealed container, and the amount of the compound of formula I is 4000-16500 mg; or
- the lyophilized formulation is contained in a sealed container with a capacity of 500 ml; the volume of the lyophilized formulation is ⅕ to ⅔, preferably ⅓ to ½ of the volume of the sealed container, and the amount of the compound of formula I is 2000-8000 mg; or
- the lyophilized formulation is contained in a sealed container with a capacity of 250 ml; the volume of the lyophilized formulation is ⅕ to ⅔, preferably ⅓ to ½ of the volume of the sealed container, and the amount of the compound of formula I is 1000-4000 mg; or
- the lyophilized formulation is contained in a sealed container with a capacity of 100 ml; the volume of the lyophilized formulation is ⅕ to ⅔, preferably ⅓ to ½ of the volume of the sealed container, and the amount of the compound of formula I is 400-2000 mg; or
- the lyophilized formulation is contained in a sealed container with a capacity of 50 ml; the volume of the lyophilized formulation is ⅕ to ⅔, preferably ⅓ to ½ of the volume of the sealed container, and the amount of the compound of formula I is 50-800 mg; or
- the lyophilized formulation is contained in a sealed container with a capacity of 30 ml; the volume of the lyophilized formulation is ⅕ to ⅔, preferably ⅓ to ½ of the volume of the sealed container, and the amount of the compound of formula I is 150-600 mg; or
- the lyophilized formulation is contained in a sealed container with a capacity of 25 ml; the volume of the lyophilized formulation is ⅕ to ⅔, preferably ⅓ to ½ of the volume of the sealed container, and the amount of the compound of formula I is 125-500 mg; or
- the lyophilized formulation is contained in a sealed container with a capacity of 20 ml; the volume of the lyophilized formulation is ⅕ to ⅔, preferably ⅓ to ½ of the volume of the sealed container, and the amount of the compound of formula I is 100-400 mg; or
- the lyophilized formulation is contained in a sealed container with a capacity of 18 ml; the volume of the lyophilized formulation is ⅕ to ⅔, preferably ⅓ to ½ of the volume of the sealed container, and the amount of the compound of formula I is 90-360 mg; or
- the lyophilized formulation is contained in a sealed container with a capacity of 15 ml; the volume of the lyophilized formulation is ⅕ to ⅔, preferably ⅓ to ½ of the volume of the sealed container, and the amount of the compound of formula I is 75-300 mg; or
- the lyophilized formulation is contained in a sealed container with a capacity of 10 ml; the volume of the lyophilized formulation is ⅕ to ⅔, preferably ⅓ to ½ of the volume of the sealed container, and the amount of the compound of formula I is 50-200 mg; or
- the lyophilized formulation is contained in a sealed container with a capacity of 8 ml; the volume of the lyophilized formulation is ⅕ to ⅔, preferably ⅓ to ½ of the volume of the sealed container, and the amount of the compound of formula I is 40-160 mg; or
- the lyophilized formulation is contained in a sealed container with a capacity of 7 ml; the volume of the lyophilized formulation is ⅕ to ⅔, preferably ⅓ to ½ of the volume of the sealed container, and the amount of the compound of formula I is 35-140 mg; or
- the lyophilized formulation is contained in a sealed container with a capacity of 5 ml; the volume of the lyophilized formulation is ⅕ to ⅔, preferably ⅓ to ½ of the volume of the sealed container, and the amount of the compound of formula I is 25-100 mg; or
- the lyophilized formulation is contained in a sealed container with a capacity of 3 ml; the volume of the lyophilized formulation is ⅕ to ⅔, preferably ⅓ to ½ of the volume of the sealed container, and the amount of the compound of formula I is 15-60 mg; or
- the lyophilized formulation is contained in a sealed container with a capacity of 2 ml; the volume of the lyophilized formulation is ⅕ to ⅔, preferably ⅓ to ½ of the volume of the sealed container, and the amount of the compound of formula I is 10-40 mg; or
- the lyophilized formulation is contained in a sealed container with a capacity of 1.5 ml; the volume of the lyophilized formulation is ⅕ to ⅔, preferably ⅓ to ½ of the volume of the sealed container, and the amount of the compound of formula I is 7.5-30 mg.

These small doses are appropriate for juveniles among human beings or animals of comparable size, such as pigs, rats, and dogs, or other animals of small size and low weight. The indications are not limited.

The lyophilized formulation provided by the present invention is recommended to be administered by intravenous infusion. Therefore, the drug solution needs to be reconstituted. Physiological saline (0.9%) or glucose injection (5%) is generally selected for reconstitution. For this purpose, the present invention provides an injection for intravenous injection containing TH-302, wherein the solvent is water; the solute comprises the active pharmaceutical ingredient TH-302, an isoosmotic adjusting reagent, mannitol or sucrose, tert-butanol and sodium bicarbonate; and the isoosmotic adjusting reagent is selected from glucose and sodium chloride.

The present invention also provides a method for preparing a solution of the lyophilized formulation with a high drug load, comprising the following procedures:

- Procedure 1: the prescribed amount of the active pharmaceutical ingredient TH-302 was weighed, added into an aqueous tert-butanol solution, and stirred until it was clear to obtain a first solution;
- Procedure 2: the prescribed amount of mannitol or sucrose was dissolved in an appropriate amount of water, stirred until it was clear to obtain a second solution;

Procedure 3: the first solution and the second solution were mixed and finally added with the remainder of prescribed amount of tert-butanol, and then added an appropriate amount of water to the predetermined volume, and further added the prescribed amount of sodium bicarbonate, and mixed homogenously under stirring;

wherein the content of the active pharmaceutical ingredient TH-302 in the solution of the lyophilized formulation with a high drug load is greater than 5 mg/ml and less than or equal to 500 mg/ml;

the volume percentage of tert-butanol relative to the solution of the lyophilized formulation with a high drug load is in the range of 1-99%, or the content of tert-butanol in the solution is in the range of 7.85-777.15 mg/ml;

the content of sucrose or mannitol in the solution of the lyophilized formulation with a high drug load is in the range of 20-300 mg/ml;

the mass ratio of TH-302 in the solution of the lyophilized formulation with a high drug load to sucrose or mannitol is in the range of 1: (0.5-20);

the volume ratio of tert-butanol in the aqueous tert-butanol solution is in the range of 30-90%; and the content of sodium bicarbonate in the solution of the lyophilized formulation with a high drug load is in the range of 0.01-0.10 mg/ml.

The present invention herein provides a process for preparing the lyophilized formulation.

The method for preparing the lyophilized formulation with a high drug load comprises the following procedures:

pre-lyophilization: the above drug solution is placed in a lyophilizing system and pre-lyophilized; the pre-lyophilization procedure comprises holding the temperature at 0 °C for a period of time and holding the temperature at −20 °C to −55 °C for a period of time;

primary drying: the temperature is elevated to a temperature in the range of −10 to 10 °C after pre-lyophilization and holding that temperature for a period of time, and the drying is performed by maintaining a vacuum; and secondary drying: the temperature is elevated to a temperature in the rang of 20 to 40 °C after primary drying and holding that temperature for a period of time, and the drying is performed by maintaining a vacuum.

As can be seen from the above illustrations, the lyophilized formulation was obtained by directly filling the solution into a lyophilized bottle (vial) and directly lyophilizing it in a lyophilizing device. Therefore, there is no step of sub-packaging. Accordingly, the unit package is exactly the corresponding lyophilized bottle package. The packaged gauge is closely related to the gauge of the lyophilized vial.

In particular, the numbers recited in this application may have an error of 10%. That is, the recited number being pulsed or subtracted 10% of that recited number should be considered to be within the range of the number recorded in this application. In other words, if the present application recites phrases, e.g., “the content is greater than 5 mg/ml but less than or equal to 500 mg/ml”, the actually measured content range being greater than 4.5 mg/ml and less than or equal to 550 mg/ml should also be determined as a matter of course to be equivalent to the above range.

DETAILED DESCRIPTION OF THE INVENTION

Figure 1:
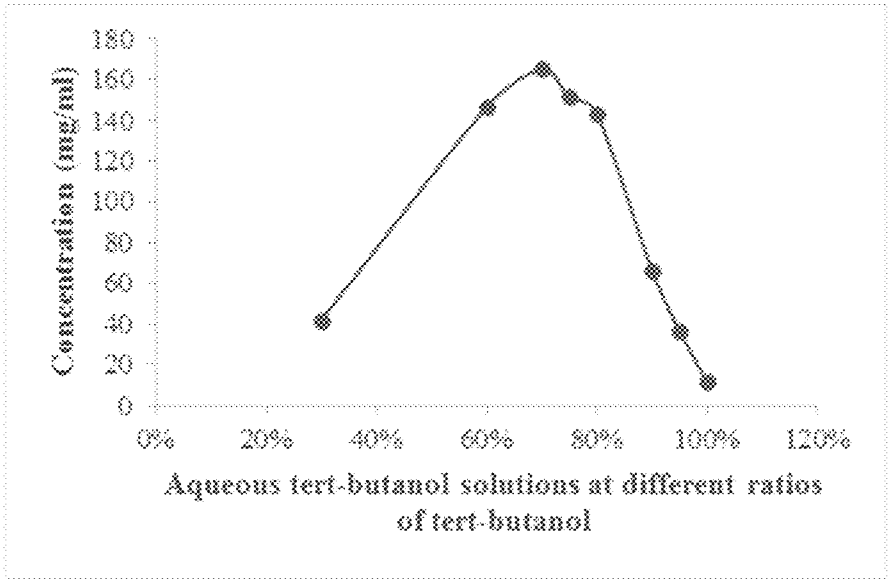
FIG. 1 shows solubility curve of TH-302 in tert-butanol aqueous solutions with different tert-butanol ratios by mass.

The present invention will be described below with reference to specific examples. Those skilled in the art could understand that these examples are only used for describing the invention and do not in any way limit its scope.

“Patient” and “individual” are used interchangeably and refer to a mammal in need of treatment for cancer. Generally, the patient is a human. Generally, the patient is a human diagnosed with cancer. In certain embodiments, a "patient" or "individual" may refer to a non-human mammal used in screening, characterizing, and evaluating drugs and therapies, such as, a non-human primate, a dog, cat, rabbit, pig, mouse or rat.

"Prodrug" refers to a compound that, after administration or application, is converted to a biologically active or more active compound (or drug) with respect to at least one property by metabolism or in other ways. A prodrug is modified chemically in a way such that it has less active or inactive relative to the drug, but the chemical modification is such that the corresponding drug is produced from the prodrug by metabolic or other biological processes after the prodrug is administered. A prodrug may have, relative to the active drug, altered metabolic stability or transport characteristics, fewer side effects or lower toxicity, or improved flavor. A prodrug may be synthesized using reactants other than the corresponding drug.

"Treatment" or "treatment of a patient" means administering, using or applying a therapeutically effective amount of the drug associated with the present invention to a patient.

"Administering", "applying" or "using" a drug to a patient refers to direct administration or application, which may be administered or applied to a patient by a medical professional or may be self-administered or applied; and/or indirect administration or application, which may be an act of prescribing a drug. For example, a physician that instructs a patient to self-administer or apply a drug or provides a patient with a prescription for a drug is administering or applying the drug to the patient.

"Therapeutically effective amount" of a drug refers to an amount of a drug that, when administered or applied to a patient with cancer, will have the intended therapeutic effect, e.g., alleviation, amelioration, palliation or elimination of one or more manifestations of cancer in the patient. A therapeutic effect does not necessarily occur by administration of one dose, and may occur only after administration of a series of doses. Thus, a therapeutically effective amount of a drug may be administered or applied one or more times.

"Treatment" of a condition or patient refers to taking steps to obtain beneficial or desired results (including clinical results). For purposes of this invention, beneficial or desired clinical results include, but are not limited to, alleviation or improvement of one or more symptoms of cancer; reduction in the severity of disease; delay or slowing of disease progression; improvement, alleviation, or stabilization of the disease state; or other beneficial results. Treatment of cancer may, in some cases, result in partial response or stable disease.

"Tumor cells" refers to tumor cells of any appropriate species, e.g., mammalian such as murine, canine, feline, equine or human.

The above description of embodiments of the present invention does not limit the present invention. Those skilled in the art can make various modifications and changes according to the present invention, and any modification and change without departing from the spirit of the present invention shall be covered in the scope of the claims appended to the present invention.

Explanations on General Information

If not otherwise specified, for each of the following experiments, the measuring or inspection methods, instruments and other information are listed as follows:

Moisture content was measured by the Karl Fischer KF method using a Mettler V10S Karl Fischer moisture meter.

The content of the residual solvent tert-butanol was measured using gas chromatography (GC). The instrument used was an Agilent 8860 gas chromatograph equipped with a 7696A automatic headspace sampler and FID detector. The chromatographic column was a capillary column packed with DB-624. GC test parameters are: a carrier gas of $N_2$; an inlet temperature of 150 °C; a detector temperature of 200 °C; a split ratio of 20:1; a temperature-elevating program with a starting temperature of 60 °C, holding of the temperature for 5 minutes, elevating the temperature to 240 °C at a rate of 30 °C/min, then running for 5 minutes at 60 °C; and headspace balancing at 85 °C for 20 minutes;

The content and concentration of TH-302 were measured using high-performance liquid chromatography (HPLC). The instrument used was Thermo Vanquish high-performance liquid chromatography. The chromatographic column was: YMC packAQ C18 4.6 mm×250 mm, 5 μm. For the detection method, please refer to the HPLC method described in the patent WO2008083101A1 owned by Threshold Pharmaceuticals Inc. (see Example 2. An Ethanol Formulation of TH302, for details).

If not otherwise specified, the symbol "/" included in the tables means not detected.

1. Solubility Experiment of TH-302

The solubility is measured in an experiment by the saturated solution method; that is, the solid TH-302 was directly charged into the solvent until insoluble matter or turbidity appears. After clarification for a period of time, the solution was directly filtered. The clarified filtrate was taken directly for determination of the concentration of TH-302. The resulting concentration is exactly the solubility of TH-302 in this solvent system. Please refer to Tables 1, 2, and 3 for specific solubility data.

For the method for measuring the concentration of TH-302 (mg/ml), please refer to the HPLC method described in the patent WO2008083101A1 owned by Threshold Pharmaceuticals Inc. (see Example 2. An Ethanol Formulation of TH302, for details); and the external standard method was used for quantification.

If the concentration is too high, the corresponding clear solution should be initially diluted to such an extent that HPLC can accurately measure it quantitatively.

When the mass ratio of tert-butanol in the data shown in Table 3 was taken as the X-axis, and the solubility of TH-302 in the tert-butanol-water mixed solvent as the Y-axis, the relationship curve shown in FIG. 1 was obtained: the active pharmaceutical drug has low solubility in the aqueous solution; as the concentration of tert-butanol in the tert-butanol aqueous solution increased, the solubility of this active pharmaceutical ingredient continued to increase; the highest solubility of the active pharmaceutical drug was reached in 70% tert-butanol aqueous solution (V/V), and then the solubility decreased as the concentration of tert-butanol in the tert-butanol aqueous solution increased.

2. Experiments for Selection of Suitable Types of Excipients (Lyo-Protectants) to be Used in Lyophilized Formulations In order to explore the feasibility of using commonly used saccharides, polyols, nonionic polymer surfactants, etc. as excipients for lyophilizing the TH-302 drug, the following excipients were selected for lyophilization experiments to investigate their stability.

Sucrose, lactose, maltose, fructose, and trehalose were selected as the saccharides.

Mannitol, glycerol and sorbitol were selected as polyols.

PVPK12 (polyvinylpyrrolidone with a molecular weight of 5500), PEG2000 (polyethylene glycol 2000), P188 (poloxamer, a polyoxyethylene polyoxypropylene ether block copolymer, brand number: 188) were selected as the nonionic polymer surfactant.

Others: SBECD (sulfobutyl ether-β-cyclodextrin), and DSPE-MPEG2000 (phosphatidylethanolamine pegol).

The drug solution for lyophilization was formulated according to Table 4 below.

TABLE 4

| Preparation Protocol of drug solutions for lyophilization prepared using different excipients 8 ml System | | | | | |
|---|---|---|---|---|---|
| Solvent | API | Protective agent | Content | API | Protective agent |
| water | 5 mg/ml | sucrose | 100 mg/ml | 40 mg | 800 mg |
| 60% | 5 mg/ml | sucrose | 100 mg/ml | 40 mg | 800 mg |
| TBA/water | 25 mg/ml | sucrose | 50 mg/ml | 2000 mg + 80 ml | 400 mg |
| (volume | 25 mg/ml | mannitol | 50 mg/ml | solvent (48 ml | 400 mg |
| ratio) | 25 mg/ml | lactose | 50 mg/ml | TBA + 32 ml $H_2O$) | 400 mg |
| | 25 mg/ml | maltose | 50 mg/ml | | 400 mg |
| | 25 mg/ml | fructose | 50 mg/ml | | 400 mg |
| | 25 mg/ml | PVPK12 | 50 mg/ml | | 400 mg |
| | 25 mg/ml | trehalose | 50 mg/ml | | 400 mg |
| | 25 mg/ml | DSPE-MPEG2000 | 50 mg/ml | | 400 mg |
| | 25 mg/ml | SBECD | 50 mg/ml | | 400 mg |
| | 25 mg/ml | PEG2000※ | 5 mg/ml | | 40 mg |
| | 25 mg/ml | P188※ | 50 mg/ml | | 400 mg |
| | 25 mg/ml | glycerol | 50 mg/ml | | 400 mg |
| | 25 mg/ml | sorbitol | 50 mg/ml | | 400 mg |

API: TH-302; TBA: tert-butanol; water: water.
※The solvent used in the experimental groups with PEG2000 and P188 protective agent is 40% TBA/water.

The TH-302 active pharmaceutical ingredient and lyoprotectant were weighed according to the above-mentioned formulation, added with the prescribed amount of tert-butanol solution, mixed homogeneously until completely dissolved, and then subpackaged (into 5 ml vials, each vial being charged with 1 ml of the drug solution, 8 vials for each formulation), and rapidly lyophilized in a small fast lyophilizer: the subpackaged formulations were pre-lyophilized at −80 °C in a ultra-low temperature refrigerator for about 2.5 hours, and then placed in a lyophilizer for about 10-90 hours (-30 °C, absolute air pressure: 0.1 mbar) to obtain a lyophilized formulation.

Experimental Results

Lyophilized powder state: white lyophilized powder cakes were successfully obtained in all the solvent groups except for those with water as the solvent. However, an oily substance appeared in the glycerol group when the lyophilizer was heated up to 0 °C Reconstitution status: for all the groups except for the sorbitol groups, reconstitution was successful (for part of them, dissolved after being shaken).

The remaining sucrose, mannitol, lactose, maltose, fructose, PVPK12, trehalose, DSPE-MPEG2000, SBECD, PEG2000, and P188 groups were subjected to high-temperature accelerated stability experiments.

After the lyophilized formulations had been removed from the lyophilizer, one of the vials was taken out at 0 °C for testing the purity by HPLC, the moisture content and the content of the residual solvents of the active pharmaceutical ingredient. The vial was then placed in a thermostat at 40 °C The purity by HPLC was tested on day 3 and day 5, respectively. The results were shown in Table 5 below.

TABLE 5

| Experimental data on accelerated stability of lyophilized formulations with different excipients at a high temperature of 40° C. | | | | | |
|---|---|---|---|---|---|
| Excipients used | Day 0 | | | Day 3 | Day 5 |
| according to the formulation | purity by HPLC | Moisture | Residual solvent | purity by HPLC | purity by HPLC |
| Sucrose (solvent: water) | 99.44% | 1.25% | ND | 96.9% | 93.02% |
| Sucrose (API: 5 mg/ml, Sucrose: 100 mg/ml) | 99.43% | 0.31% | 59.20% | 97.37% | 93.60% |
| Sucrose (API: 25 mg/ml, Sucrose: 50 mg/ml) | 99.40% | 0.32% | 4.89% | 95.51% | 92.85% |
| Mannitol | 99.34% | 0.49% | 2.13% | 97.81% | 97.76% |
| Lactose | 99.30% | 0.85% | 1.57% | 94.77% | 91.47% |
| Maltose | 99.39% | 0.70% | 2.94% | 95.45% | 92.47% |
| Fructose | 99.31% | 0.61% | 2.43% | 96.91% | 96.87% |
| PVPK12 | 99.29% | 0.63% | 7.70% | 95.35% | 92.28% |
| Trehalose | 99.42% | 0.46% | 2.89% | 95.47% | 94.69% |

TABLE 5-continued

Experimental data on accelerated stability of lyophilized formulations with different excipients at a high temperature of 40° C.

| Excipients used according to the formulation | Day 0 purity by HPLC | Day 0 Moisture | Day 0 Residual solvent | Day 3 purity by HPLC | Day 5 purity by HPLC |
|---|---|---|---|---|---|
| DSPE-MPEG2000 | 99.31% | 0.37% | ND | 98.43% | 98.22% |
| SBECD | 99.40% | 0.55% | 7.12% | 97.87% | 98.10% |
| PEG2000 | 98.73% | 0.59% | ND | 98.93% | 99.01% |
| P188 | 99.04% | 0.68% | 6.19% | 98.71% | 98.76% |

ND: Not detected

Figure 2:
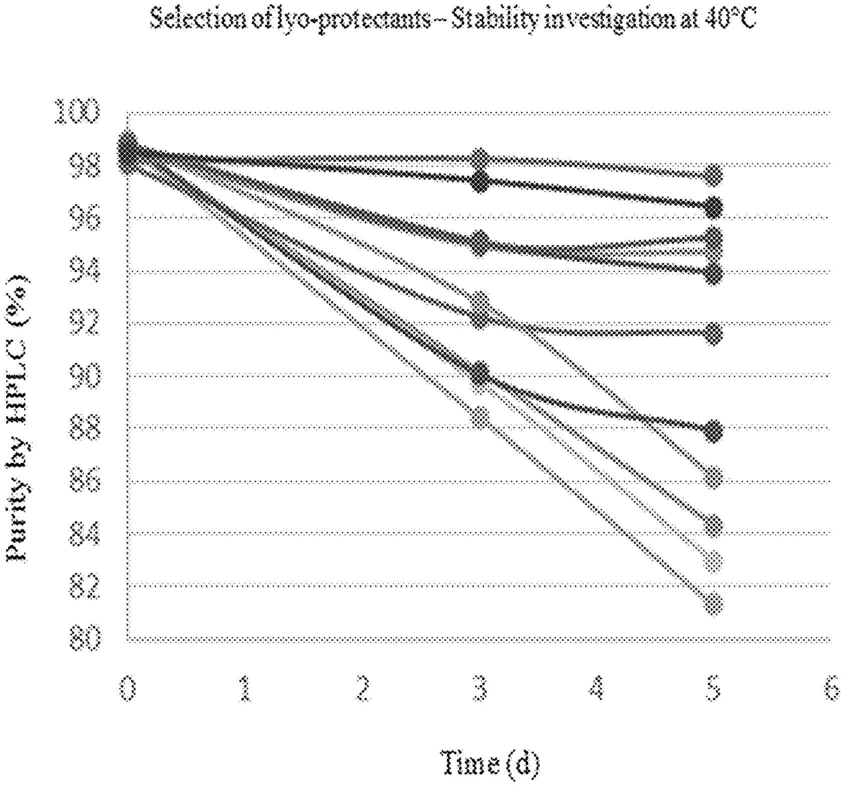
FIG. 2 shows stability curves of lyophilized formulations prepared with 11 excipients over 5 days. These curves, distinguished by the rightmost circles, from top to bottom, are curves of lyophilized formulations prepared with PEG2000, P188, SBECD, mannitol, DSPE-MPEG2000, fructose, trehalose, PVPK12, sucrose, maltose, and lactose, respectively.

The curve of FIG. 2 was obtained by using the data in Table 5 with the number of days as the X-axis and the purity by HPLC as the Y-axis.

Experimental Conclusion

Generally speaking, the selection of a lyoprotectant for injection should take into account the following factors: good stability; can be conventionally used; and will not affect the drug efficacy, DMPK, and toxicology. By analyzing the curve in FIG. 2, it can be seen that PEG2000 is used non-conventionally; and P188/SBECD/DSPE-MPEG2000 may affect the efficacy, DMPK and toxicological effect. Generally speaking, mannitol is an ideal excipient, and sucrose also has potential for development (it is likely to improve stability and reduce tert-butanol residue by optimizing the amount and lyophilizing conditions).

Figure 3:
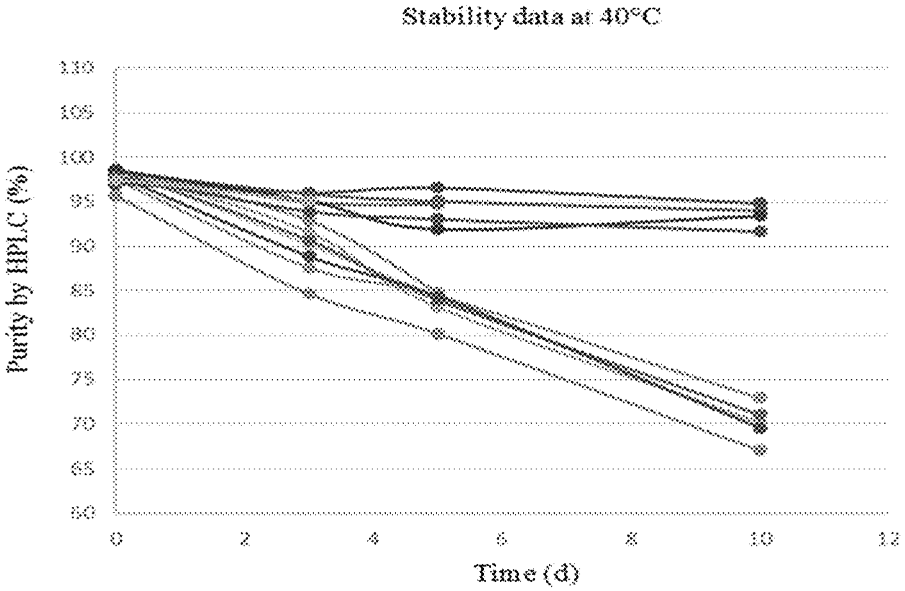
FIG. 3 shows stability curves of lyophilized formulations prepared with sucrose and mannitol as excipients over 10 days. The four upper curves in the figure are those of lyophilized formulations prepared with mannitol, and the lower four curves are those of lyophilized formulations prepared with sucrose.

In order to further evaluate the stability of mannitol and sucrose, the purity by HPLC was tested after the mannitol and sucrose samples had been stored for 10 days, and the results were plotted into a curve, as shown in FIG. 3.

By analyzing the curve of FIG. 3, it can be seen that under the preliminary formulation conditions shown in Table 4, the stability of formulation with mannitol is better than that with sucrose.

3. Experiments for Investigating the Effects of Different Lyo-Protectants (100 mg/ml Sucrose or 80 mg/ml Mannitol) on the Stability of the Lyophilized Powder and the Reconstituted Solution Based on their experiences and the use of similar lyophilized formulation drugs, the inventors have initially determined to use 100 mg/ml sucrose and 80 mg/ml mannitol as excipients to investigate the stability of the prepared lyophilized formulation of TH-302 and the stability of the reconstituted solution.

3.1 Experiments on the Storage Stability of Lyophilized Formulations at Room Temperature and Accelerated at High Temperatures The drug solution for lyophilization was formulated according to Table 6 below. 40 vials for each group were prepared, 1 ml/vial; and a total of 40 ml drug solution was prepared for each formulation.

TABLE 6

Preparation Protocol of drug solutions for lyophilization prepared using 100 mg/ml sucrose and 80 mg/ml mannitol as excipients

| Tert-butanol Volume ratio % | Tert-butanol Volume/ml | Water Volume/ml | Lyoprotectant Content | Lyoprotectant Actual weight/g | API Content | API Actual weight/g | pH |
|---|---|---|---|---|---|---|---|
| 40% | 16 | 24 | Sucrose 100 mg/ml | 4.039 | 25 mg/ml | 0.999 | 7.13 |
| 40% | 16 | 24 | Mannitol 80 mg/ml | 3.203 | 20 mg/ml | 0.716 | 7.31 |

Process for Preparing the Drug Solution:

1. The prescribed amount of lyo-protectant was initially dissolved in the prescribed amount of water until it was completely dissolved.

2. The prescribed amount of tert-butanol was added into the aqueous lyo-protectant solution and mixed homogeneously. Then the prescribed amount of API was added and stirred until it was completely dissolved.

3. The pH of the drug solution formulated with sucrose was measured to be 4.24, and it was adjusted with 10 μL of $NaHCO_3$ injection to 6.43. Another 10 μL of the injection was added to adjust the pH to 7.13.

The pH of the drug solution formulated with mannitol was measured to be 4.62, and it was adjusted with 12 μL of $NaHCO_3$ injection to 7.31.

The resulting solution was filtered with PVDF and subpackaged in 1 ml/vial.

An operation similar to the aforementioned "fast lyophilization" was used and the relevant parameters were adjusted to obtain a lyophilized formulation.

After lyophilization, the vials were stoppered under vacuum and crimp-capped. The lyophilized formulation was obtained. The residual solvent and moisture in the lyophilized formulation were measured.

The lyophilized formulation samples were placed in a thermostat at 25 °C or 40 °C, and the purity by HPLC was measured on the corresponding days. The results were shown in Table 7 below.

TABLE 7

Stability experimental data of lyophilized samples prepared with 100 mg/ml sucrose and 80 mg/ml mannitol as excipients at high temperature of 40° C. and room temperature of 25° C.

| Excipients used in | Day 0 | | | | Day 3 | | Day 5 | | Day 10 | |
|---|---|---|---|---|---|---|---|---|---|---|
| | purity by HPLC | | Moisture | Residual solvent | purity by HPLC | | purity by HPLC | | purity by HPLC | |
| | Storage temperature | | | | | | | | | |
| the formulation | 25° C. | 40° C. | 25° C. | 25° C. | 25° C. | 40° C. | 25° C. | 40° C. | 25° C. | 40° C. |
| Sucrose 100 mg/ml | 99.22% | NA | 0.77% | 8.23% | NA | 95.81% | 98.46% | 93.09% | 97.69% | 85.07% |
| Mannitol 80 mg/ml | 99.04% | NA | 0.72% | 0.84% | NA | 97.35% | 98.35% | 97.00% | 98.38% | 96.42% |

NA: Not analyzed

Figure 4:
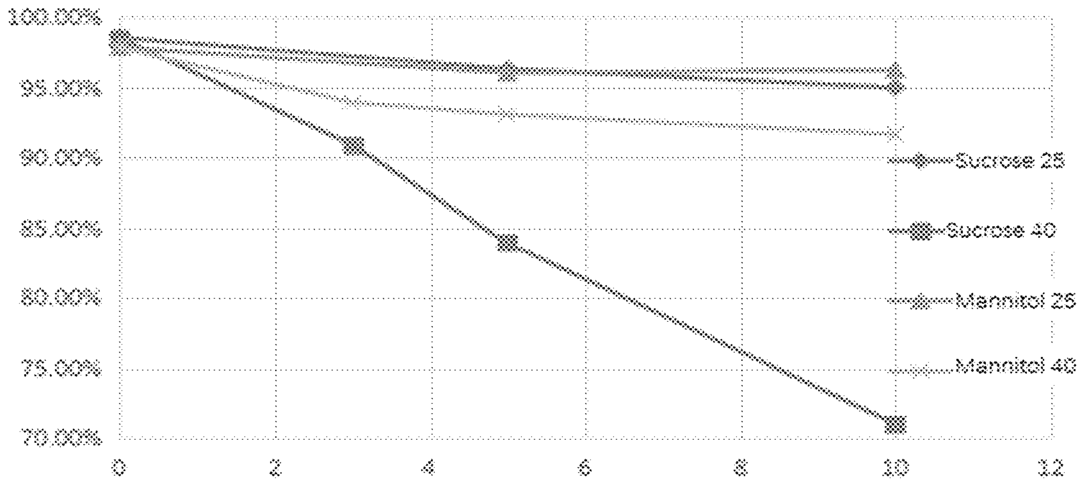
FIG. 4 shows stability curves of lyophilized samples prepared with 100 mg/ml sucrose and 80 mg/ml mannitol as excipients at a high temperature of 40 °C and at room temperature of 25 °C. The abscissa represents the number of days, and the ordinate represents the purity by percentage measured by HPLC.

The stability curves with 100 mg/ml sucrose and 80 mg/ml mannitol were plotted using the purity by HPLC in Table 7 as the Y-axis and time as the X-axis, and were shown in FIG. 4.

By analyzing and comparing the data shown in Table 7 and FIG. 4, it can be concluded that the stability of lyophilized formulation samples formulated using a drug solution with mannitol as an excipient at 25 °C or 40 °C is better than that of those formulated with sucrose.

3.2 Reconstitution Stability and Combination Experiments of Lyophilized Formulations One vial of the lyophilized powder was taken and dissolved with D5W (dextrose 5% by mass in water) to obtain a solution containing about 5 mg of API per 1 mL. Then, the obtained solution was left to stand at room temperature. The color and clarity of the solution were determined at 0, 6, and 24 hours, respectively. The results showed that a colorless, transparent, and clear solution was observed in all of the cases.

The solution was diluted with 30% acetonitrile in water at 0, 6, and 24 hours respectively to a solution containing about 1 mg of API per 1 mL, which was measured for purity by HPLC. The results were shown in Table 8 below.

TABLE 8

Stability experimental data of lyophilized samples prepared with 100 mg/ml sucrose and 80 mg/ml mannitol as excipients at room temperature of 25° C.

| Lyophilized formulation- time | Diluted multiple | Measured concentration(mg/ml) | purity by HPLC |
|---|---|---|---|
| 100 mg/ml sucrose-0 h | 25 | 0.9615 | 98.61% |
| 100 mg/ml sucrose-6 h | 25 | 0.9570 | 98.36% |
| 100 mg/ml sucrose-24 h | 25 | 0.9713 | 98.25% |
| 80 mg/ml mannitol -0 h | 20 | 0.9549 | 97.84% |
| 80 mg/ml mannitol-6 h | 20 | 0.9730 | 97.68% |
| 80 mg/ml mannitol-24 h | 20 | 0.9544 | 97.05% |

One vial of the lyophilized powder was taken and dissolved with D5W to obtain a solution containing about 5 mg of API per 1 mL. The pH value and osmotic pressure of the obtained solution were measured. The results were shown in Table 9 below. During the measurement, the pH value and osmotic pressure of 5% dextrose injection were also measured.

TABLE 9 pH value and osmotic pressure data of lyophilized samples prepared with 100 mg/ml sucrose and 80 mg/ml mannitol as excipients respectively after reconstituted with D5W at room temperature 25° C.

| Formulation | 100 mg/ml Sucrose | 80 mg/ml Mannitol | 5% Dextrose |
|---|---|---|---|
| pH value | 5.14 | 5.05 | 5.47 |
| Osmotic pressure | 344 mOsmol/kg | 374 mOsmol/kg | 259 mOsmol/kg |

After comparison, it was found that in terms of the stability and combination of the reconstituted lyophilized formulations, there is not much difference between the results of the formulation with the 100 mg/ml sucrose and formulation with 80 mg/ml mannitol. Both of them can meet the requirements.

By comprehensively considering the storage stability experiments of lyophilized formulations at room temperature and under high temperature acceleration and the stability and combination experiments of reconstituted lyophilized formulations, it can be seen that, under the existing rapid lyophilizing process conditions, the lyophilized formulation samples prepared using a drug solution containing mannitol as an excipient had better stability at 25 °C and 40 °C than those formulated with sucrose, while the stability and combination of the reconstituted with 5% dextrose injection was only slightly different.

4. Experiments for Investigating the Effects of the pH and API Concentration of the Intermediate Drug Solution on Sample Reconstitution The drug solution for lyophilization was formulated according to Table 10 below.

TABLE 10

Preparation Protocol for lyophilized drug solution to investigate the effects of API concentration and pH on sample reconstitution

| Formulation Batch No. | Volume of the formulated solution | Tert-butanol-volume ratio 40% Weight/g | Water-volume ratio about 60% Weight/g | Lyo-protectant-80 mg/ml mannitol Weight/g | API Content | API Actual weight/g | pH |
|---|---|---|---|---|---|---|---|
| 01 | 200 ml | 62.801 | 100.195 20.107 | 16.024 | 15 mg/ml | 3.000 | / |
| 02 | 150 ml | 47.106 | 80.983 10.306 | 12.010 | 20 mg/ml | 3.073 | / |
| 03 | 200 ml | 62.833 | 100.460 20.28 | 16.020 | 15 mg/ml | 3.046 | 7.13 |
| 04 | 150 ml | 47.144 | 80.584 10.063 | 12.002 | 20 mg/ml | 3.057 | 7.03 |

The density of tert-butanol is p=0.785 g/ml. Thus, the 40% volume ratio of tert-butanol in 200 ml of the drug solution corresponds to tert-butanol volume of 80 ml and tert-butanol mass of 62.80 g.

Process for Preparing the Drug Solution:

1. The prescribed amount of lyo-protectant was initially dissolved in an amount, which is about 80% of the prescribed amount, of water under stirring until it was completely dissolved.

2. The prescribed amount of API was added to tert-butanol and the remaining water, and dissolved under stirring.

3. The solutions obtained from the above two steps were mixed homogeneously.

4. The mixed solution was filtered. The pH values of the solutions for 01 and 02 batches were not adjusted, while the pH values of the solutions for 03 and 04 batches were adjusted to 7.0.

5. Filling: for batch 01, filled with 14 mL; for batch 02, filled with 10.5 mL; for batch 03, filled with 14 mL; and for batch 04, filled with 10.5 mL. The gauge of the filling vial is 50 mL.

Figure 5:
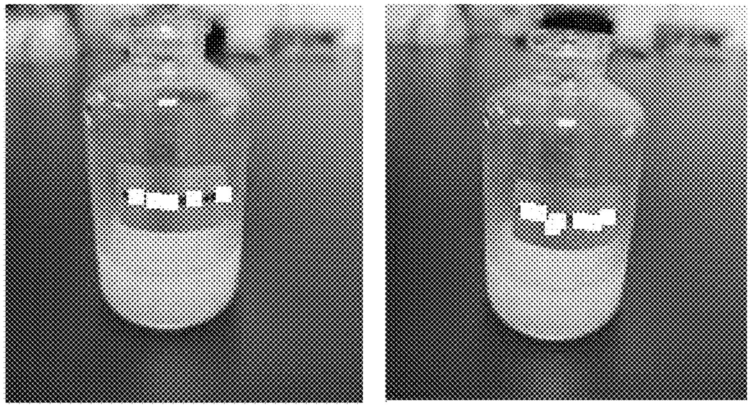
FIG. 5 shows a photograph of drug solution samples. The drug solution samples have been crystallized in an environment at 2-° C. at the bottom of the bottles containing the drug solution samples. The labels have been covered by mosaic.

One vial from each of the batches 01, 02, 03, and 04 was placed in a medical-grade refrigerator (2-8 °C), and observed for crystallization phenomenon: it was found that they all exhibited varying degrees of crystallization, as shown in FIG. 5 below. The crystallization supernatant of batch 01 and reconstituted solution of the crystals (reconstituted with 5% dextrose solution) were taken, and measured for their API contents. The results were shown in Table 11 below.

TABLE 11

Contents and purities by HPLC of the reconstituted solution and supernatant after the intermediate drug solution being placed for 01 batch at 2-8° C.

| Sample batch No. | Measured concentration(mg/ml) | purity by HPLC |
|---|---|---|
| The reconstituted solution after batch 01 intermediate drug solution being placed at 2-8° C. | 13.4909 | 99.30 |
| Batch 01: supernatant after batch 01 intermediate drug solution being placed at 2-8° C. | 14.0239 | 99.30 |

Figure 6:
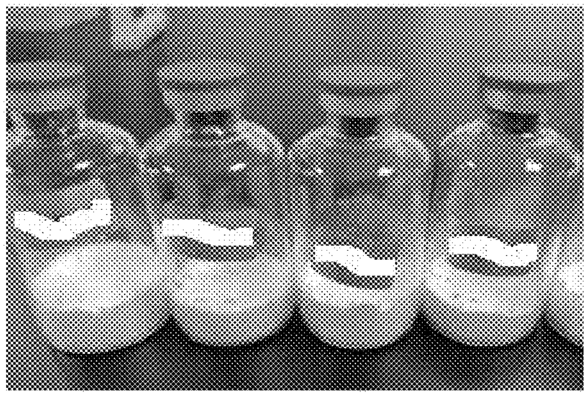
FIG. 6 shows a photograph of four batches of lyophilized formulations. In the photograph, batches 01, 02, 03, and 04 of lyophilized formulations are shown respectively from left to right. The labels have been covered by mosaic.

The above-mentioned filled formulations were lyophilized in a vacuum lyophilizer. The lyophilizing conditions, which were optimized in multiple times, were used, and were shown in Table 12 below. After lyophilization, the vials were stoppered under vacuum and then crimp-capped. The lyophilized formulations as shown in FIG. 6 were obtained.

TABLE 12

Lyophilizing conditions after multiple optimizations

Pre-lyophilizing

| Stage | Set temperature (° C.) | Set time (min) | Duration (min) |
|---|---|---|---|
| 1 | 0.0 | 0.5~2 | 60 |
| 2 | −20~−55 | 0.5~2 | 120~1200 |

| Stage | Primary drying Temperature (° C.) | Primary drying Set time (min) | Primary drying Duration (min) | Primary drying Vacuum (mbar) | Secondary drying Temperature (° C.) | Secondary drying Set time (min) | Secondary drying Duration (min) | Secondary drying Vacuum (mbar) |
|---|---|---|---|---|---|---|---|---|
| 1 | −10~10 | 120~360 | 400~800 | 0.2 | 20~40 | 30~150 | 400~1200 | 0.2 |

The above lyophilized formulations were reconstituted with 40 ml and 50 ml of 5% dextrose solution, respectively. Results were shown in Table 13 below.

TABLE 13

| Phenomena observed by visual for formulations after reconstitution with 40 ml and 50 ml of 5% dextrose solution, respectively | | |
|---|---|---|
| Batch | Reconstituted with 40 ml of 5% dextrose solution Phenomenon | Reconstituted with 50 ml of 5% dextrose solution Phenomenon |
| 01 | no adhesions on the vial wall but a few insoluble particles at the vial bottom | no adhesions on the vial wall but a few insoluble particles at the vial bottom |
| 02 | a few adhesions on the vial wall and insoluble particles at the vial bottom | no adhesions on the vial wall but a few insoluble particles at the vial bottom |
| 03 | no adhesions on the vial wall but a few insoluble particles at the vial bottom; after being left to stand for a period of time, the solution became clear | no adhesions on the vial wall and no insoluble particles at the vial bottom; and the solution is clear |
| 04 | a few adhesions on the vial wall and insoluble particles at the vial bottom | no adhesions on the vial wall but very few insoluble particles at the vial bottom |

Figure 7:
FIG. 7 shows comparison photographs of 4 batches of lyophilized formulation samples with 40 ml of 5% dextrose solution in the reconstitution experiment after the solution was added with those after standing was performed. The left photograph shows the samples added with the solution, and the right photograph shows the samples after standing was performed. From left to right in each of the photographs, there are batches 01, 02, 03, and 04. The labels have been covered by mosaic.

The photographs of the formulations reconstituted with 40 ml of 5% dextrose solution were shown in FIG. 7, wherein for batch 3 (with the concentration of API being 15 mg/ml, and the pH being adjusted to 7.13), there were no adhesions on the vial wall and a few insoluble particles at the vial bottom. After being left to stand for a period of time, the solution became clear, indicating that excessively high concentration of API may be detrimental to subsequent reconstitution of the lyophilized formulation.

Figure 8:
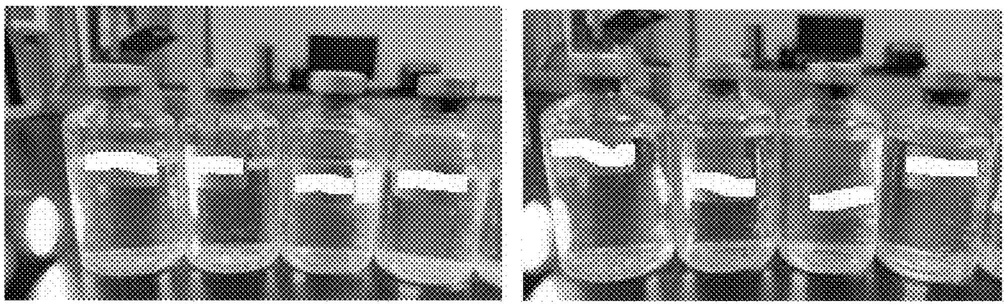
FIG. 8 shows comparison photographs of 4 batches of lyophilized formulation samples with 50 ml of 5% dextrose solution in the reconstitution experiment after the solution was added with those after standing was performed. The left photograph shows the samples added with the solution, and the right photograph shows the samples after standing was performed. From left to right in each of the photographs, there are batches 01, 02, 03, and 04. The labels have been covered by mosaic.

The photographs of the formulations reconstituted with 50 ml of 5% dextrose solution were shown in FIG. 8, wherein for batch 3 (with the concentration of API being 15 mg/ml, and the pH being adjusted to 7.03), there were no adhesions on the vial wall and no insoluble particles at the vial bottom, and the solution is clear, indicating that an increased volume of the solution for reconstitution can improve the reconstituted lyophilized formulation.

Experimental Conclusion

By comparing the experimental results, the inventors have found that although the solubility of API (TH-302) in the tert-butanol-water mixed solvent system can be up to 160 mg/ml or more, the concentration of API should be within a suitable range because:

First, an excessively high concentration of API may cause crystallization and stratification for the drug solution during the cooling procedure of the lyophilizing process, thereby affecting the lyophilizing process;

Second, an excessively high concentration of the drug may affect the reconstitution, leading to the failure of reconstitution.

Thus, there is a suitable range of API concentration. After extensive experimentation, the inventors have found that the range of 5-160 mg/ml is preferably suitable, or further the API concentration of 8-50 mg/ml may result in a stable drug solution and good quality of the subsequently lyophilized formulation.

5. Experiment for Investigating the Effects of API Concentration, Lyo-Protectant Concentration, and Tert-Butanol Concentration on the Residual Solvent of the Lyophilized Powder The effects of API concentration, lyo-protectant concentration, and tert-butanol concentration on the residual solvent of the lyophilized powder were investigated, and a blank lyophilized powder was formulated and used as a control.

The drug solution for lyophilization was prepared according to Table 14 below. 10 Vials for each batch, 1 mL/vial, 10 mL in total.

TABLE 14

Preparation for lyophilized drug solution for investigation of the effects of API concentration, lyo-protectant concentration, and tert-butanol concentration on the residual solvent of the lyophilized powder

| | Formulation | | | | | | |
|---|---|---|---|---|---|---|---|
| | Tert-butanol | | Lyo-protectant | | API | | Water |
| Batch No. | Volume ratio | Volume/ ml | Content | Actual weight/g | Content | Actual weight/g | Volume/ ml |
| 01 | 40% | 4 | Sucrose 100 mg/ml | 1.014 | 25 mg/ml | 0.251 | 6 |
| 02 | 40% | 4 | Mannitol 80 mg/ml | 0.806 | 20 mg/ml | 0.200 | 6 |
| 03 | 60% | 6 | Sucrose 100 mg/ml | 1.029 | 25 mg/ml | 0.251 | 4 |
| 04 | 60% | 6 | Mannitol 40 mg/ml | 0.411 | 20 mg/ml | 0.201 | 4 |
| 05 | 0% | 0 | Sucrose 100 mg/ml | 1.000 | 5 mg/ml | 0.054 | 10 |
| 06 | 40% | 4 | Sucrose 100 mg/ml | 1.010 | 0% | 0 | 6 |
| 07 | 40% | 4 | Mannitol 80 mg/ml | 0.805 | 0% | 0 | 6 |

Process for Preparing a Drug Solution:

1. The prescribed amount of lyo-protectant was initially dissolved in the prescribed amount of water until it was completely dissolved.

2. For batches 01, 02, 03 and 04, the prescribed amount of tert-butanol was added into the aqueous lyo-protectant solution and mixed homogeneously. Then the prescribed amount of API was added and stirred until it was completely dissolved.

For batch 05, no tert-butanol was added. The prescribed amount of API was added and stirred until it was completely dissolved.

For batches 06 and 07, the prescribed amount of tert-butanol was added into the aqueous lyo-protectant solution and mixed homogeneously. They were not added with API and were used as blank controls.

3. In this experiment, the pH was not adjusted, and the solution was subpackaged into 1 ml/vial.

Figure 9:
FIG. 9 shows a sample photograph of seven batches of lyophilized formulations. From left to right, there are batches 01 to 07. The labels have been covered by mosaic.

The above-mentioned subpackaged formulations were pre-lyophilized in a refrigerator at −70 °C for 3 hours, and then dried in a lyophilizer for 62 hours. After lyophilization, the vials were stoppered under vacuum and then crimp-capped. The lyophilized formulation as shown in FIG. 9 was obtained.

The formulation was injected with D5W for reconstitution. For all batches to 07, the reconstitution was easy and the solutions were clear.

The lyophilized formulation samples were placed in a thermostat at 40 °C, and the purity by HPLC was measured on the corresponding days. The results were shown in Table 15 below.

TABLE 15

Purity by HPLC data (%) of the lyophilized samples for five batches at high temperature of 40° C.

| Bacth No. | Day 0 | Day 3 | Day 5 | Day 10 |
|---|---|---|---|---|
| 01 | 99.07% | 94.94% | 92.84% | 85.68% |
| 02 | 98.54% | 98.34% | 98.40% | 98.19% |
| 03 | 99.25% | 94.95% | 93.02% | 85.83% |
| 04 | 99.17% | 98.25% | 97.96% | 97.76% |
| 05 | 98.76% | 92.63% | 90.50% | 83.75% |

The tert-butanol (2 vials) and moisture (1 vial) contents of the samples on day 0 were also measured.

The results were shown in Tables 16 and 17 below.

TABLE 16

Residual tert-butanol content data of 7 batches lyophilized samples determined on day 0

| Test date | Sample name | Sample Batch No. | Percent by mass | Trait |
|---|---|---|---|---|
| Dec. 9, 2021 | lyophilized formulation | 01 middle | 11.95% | White lyophilized cake |
| | lyophilized formulation | 02 middle | 0.73% | |
| | lyophilized formulation | 03 middle | 12.17% | |
| | lyophilized formulation | 04 middle | 0.46% | |
| | lyophilized formulation | 05 middle | ND | |
| | lyophilized formulation | 06 middle | 0.3168 mg/vial | |
| | lyophilized formulation | 07 middle | 0.0184 mg/vial | |
| | lyophilized formulation | 01 lower | 13.19% | |
| | lyophilized formulation | 02 lower | 5.10% | |
| | lyophilized formulation | 03 lower | 16.15% | |
| | lyophilized formulation | 04 lower | 2.53% | |
| | lyophilized formulation | 05 lower | 0.21% | |
| | lyophilized formulation | 06 lower | 0.3107 mg/vial | |
| | lyophilized formulation | 07 lower | 0.0271 mg/vial | |

Note: For batch 05, TBA was not added. “01 middle” and “01 lower” represent the lyophilized formulation samples obtained by lyophilizing the drug solutions, which were from the same batch and placed on different plates (middle and lower layers) in the lyophilizer.

TABLE 17

Residual water content data of 7 batches lyophilized samples determined on day 0

| Bactch No. | Sample size/g | Percent by mass (%) | Notes |
|---|---|---|---|
| 01 | 0.11306 | 0.78 | / |
| 02 | 0.08453 | 0.63 | During the measurement, the sample appeared to be white and turbid. |
| 03 | 0.10365 | 0.66 | / |
| 04 | 0.05507 | 0.39 | / |
| 05 | 0.08255 | 1.79 | / |
| 06 | 0.08618 | 1.06 | / |
| 07 | 0.06077 | 0.46 | During the measurement, the sample appeared to be white and turbid. |

Experimental Conclusions

In the samples prepared by the small lyophilizer, the TBA residues in the samples in each vial were at varying levels, and the residual TBA contents in those formulated with sucrose were higher than those formulated with mannitol.

Under the condition of 40 °C, the amount of related substances in those formulated with sucrose increased largely, while the amount of the related substances in those formulated with mannitol increased slightly.

The API concentration does not have much relationship with the residual solvent content in the lyophilized formulation. Likewise, the lyo-protectant concentration does not have much relationship with the residual solvent content in the lyophilized formulation.

The API concentration, lyo-protectant concentration, and tert-butanol concentration all affect the residual solvent content in the lyophilized formulation: in comparison, the lyophilized formulation obtained by using mannitol as a lyo-excipient (lyo-protectant) has low residual level, and in stability experiments accelerated at high temperature, the formulations formulated with mannitol have better stability than those formulated with sucrose.

6. Experiments for Investigating the Effects of Different API Concentrations and Mannitol Concentrations, Different Proportions of Tert-Butanol, and Different Filled Volumes on Sample Reconstitution 6.1 Investigating the Effects of Different pH Values and Filled Amounts of the Formulations (40% Tert-Butanol+60 mg/ml Mannitol+10 mg/ml API) on Sample Reconstitution A 600 ml drug solution was prepared according to Table 18.

TABLE 18

Preparation of lyophilized drug solution for investigation of effects of different pH values and filled amounts of the formulation (40% tert-butanol + 60 mg/ml mannitol + 10 mg/ml API) on sample reconstitution

| | Formulation | | | | | | | | |
|---|---|---|---|---|---|---|---|---|---|
| | Tert-butanol | | Water | | Lyoprotectant | | API | | |
| Bacth No. | Volume ratio | Weighed amount/g | Volume ratio | Weighed amount/g | Content | Weighed amount/g | Content | Actual weight/g | pH |
| A (drug solution) | 40% | 188.435 | 60% | 200.620 g 160.446 g | Mannitol 60 mg/ml | 36.056 | 10 mg/ml | 6.029 | |
| 01 (lyophilized formulation) | 300 ml: pH not adjusted | | | | Filled with 10.5, 16, and 21 ml respectively | | | | / |
| 02 (lyophilized formulation) | 300 ml: pH adjusted | | | | Filled with 10.5, 16, and 21 ml respectively | | | | 7.07 |

Density of tert-butanol is p=0.785 g/ml; thus, the volume of 240 ml corresponds to 188.4 g.

Process for Preparing the Drug Solution:

1. The prescribed amount of tert-butanol was added under stirring to the aqueous lyo-protectant solution and mixed homogeneously. Then the prescribed amount of API was added and dissolved under stirring.

2. Filtered using a sterile filter cup. Batch 01: 300 ml, no pH adjustment; Batch 02: pH 4.58, which was adjusted to 7.07; at the same time, 6 ml of solution for each batch was taken and stored in a refrigerator (2~8 °C) to observe the crystallization phenomenon.

3. Filling:

200 mg/vial: for batch 01, filled with 21 mL to give 6 vials; and for batch 02, filled with 21 mL to give 6 vials;

150 mg/vial: for batch 01, filled with 16 mL to give 6 vials; and for batch 02, filled with 16 mL to give 6 vials;

100 mg/vial: for batch 01, filled with 10.5 mL to give 6 vials; and for batch 02, filled with 10.5 mL to give 6 vials.

6.2 Investigation of the Effects of Different pH Values and Filled Amounts of the Formulations (30% Tert-Butanol+70 mg/ml Mannitol+12.5 mg/ml API) on Sample Reconstitution A 600 ml drug solution was prepared according to Table 19.

TABLE 19

Preparation of lyophilized drug solution for investigation of the effects of different pH values and filled amounts of the formulations (30% tert-butanol + 70 mg/ml mannitol + 12.5 mg/ml API) on sample reconstitution

| | Formulation | | | | | | | | |
|---|---|---|---|---|---|---|---|---|---|
| | Tert-butanol | | Water | | | | API | | |
| | Volume | | Volume | | Lyoprotectant | | | Actual | |
| Batch No. | ratio % | Weight/g | ratio % | Weight/g | Content | Weight/g | Content | weight/g | pH |
| B(drug solution) | 30% | 141.367 | 70% | 220.232 g 200.145 g | Mannitol 70 mg/ml | 42.019 | 12.5 mg/ml | 7.532 | / |
| 03 (lyophilized formulation) | 300 ml: pH not adjusted | | | | filled with 8.5, 13 and 17 ml vials respectively | | | | / |
| 04 (lyophilized formulation) | 300 ml: pH adjusted | | | | filled with 8.5, 13 and 17 ml vials respectively | | | | 7.01 |

Density of tert-butanol is p=0.785 g/ml, then the corresponding mass of tert-butanol in 180 ml is 141.3 g.

Process for Preparing a Drug Solution:

1. The prescribed amount of lyo-protectant was initially dissolved in about prescribed amount of water under stirring at 500 rpm until it was completely dissolved.

2. The prescribed amount of tert-butanol was added to the aqueous lyo-protectant solution and mixed homogeneously. Then the prescribed amount of API was added and dissolved under stirring.

3. Filtered using a sterile filter cup. Batch 03: 300 ml, no pH adjustment; Batch 04: pH 4.61, which was adjusted to 7.01; at the same time, 6 ml of the solution for each batch was taken and stored in a refrigerator (2~8 °C) to observe the crystallization phenomenon;

4. Filling:

200 mg/vial: for batch 03, filled with 17 mL to give 8 vials; and for batch 04, filled with 17 mL to give 8 vials;

150 mg/vial: for batch 03, filled with 13 mL to give 7 vials; and for batch 04, filled with 13 mL to give 7 vials;

100 mg/vial: for batch 03, filled with 8.5 mL to give 8 vials; and for batch 04, filled with 8.5 mL to give 8 vials;

6.3 Pre-Lyophilization and Lyophilization

The above-mentioned subpackaged formulations were lyophilized in a vacuum lyophilizer. The lyophilization was performed using the parameters listed in Table 12. After lyophilization, the vials were stopperd under vacuum and then crimp-capped. The lyophilized formulations were obtained.

6.4 Experimental Results (1) Crystallization Phenomenon in the Intermediate Drug Solutions 6 ml of the solutions from batches 01 and 02 were taken and stored in a refrigerator (2-8 °C) for a period of time (2 hours). Then, the solutions was clear and no crystallization was observed.

6 ml of the solutions from batches 03 and 04 were taken and stored in a refrigerator (2-8 °C) for a period of time (2 hours). Then, crystallization was observed.

(2) Sample Reconstitution

All the lyophilized formulations were white cakey solids.

The solvents used for reconstituting the samples and the phenomena after reconstitution were shown in Table 20 below.

TABLE 20

Experimental results showing the effects of different API concentrations and mannitol concentrations, different proportions of tert-butanol, and different filled volumes on sample reconstitution Sample reconstitution

| Sample Batch No. (filled volume) | Volume/ml of purified water for reconstitution | Phenomenon after reconstitution |
|---|---|---|
| 01(21 ml) | 30 ml | minor adhesions on the vial wall and insoluble materials at the vial bottom. |
| | 40 ml | minor adhesions on the vial wall |
| | normal pressure, 45 ml | minor adhesions on the vial wall and no insoluble particles at the vial bottom; and the solution being clear |
| 01(16 ml) | 35 ml | very few adhesions on the vial wall |
| | normal pressure, 35 ml | clear solution |
| 01(10.5 ml) | 30 ml | clear solution |
| 02(21 ml) | normal pressure, 45 ml | clear solution |
| | 40 ml | minor adhesions on the vial wall and the solution being clear |
| 02(16 ml) | 40 ml | clear solution |
| | 30 ml | minor adhesions on the vial wall and the solution being clear |
| 03(13 ml) | normal pressure, 45 ml | minor adhesions on the vial wall and the solution being clear |
| | 30 ml | minor adhesions on the vial wall and insoluble particles at the vial bottom. |
| | 40 ml | minor adhesions on the vial wall and the solution being clear |
| | 30 ml | very few adhesions on the vial wall |
| | 40 ml | clear solution |
| 03(8.5 ml) | 22 ml | minor adhesions on the vial wall and the solution being clear |
| 04(17 ml) | normal pressure, 45 ml | minor adhesions on the vial wall and the solution being clear |
| | 40 ml | very few adhesions on the vial wall and the solution being clear |
| 04(13 ml) | 30 ml | minor adhesions on the vial wall and the solution being clear |
| 04(8.5 ml) | 22 ml | clear solution |

Normal pressure means the condition under which purified water was injected into a vial containing the lyophilized formulation for reconstitution when it is in communication with the external environment after the aluminum cap and rubber stopper of the vial has been opened; and normal pressure being not indicated means the condition under which purified water was directly injected into the vial containing the lyophilized formulation via a syringe (in this case, the air pressure inside the vial is lower than the external atmospheric pressure) for reconstitution.

Samples from batch 04 (8.5 ml, 13 ml, and 17 ml) were taken after being stored at 40 °C for 10 days and then reconstituted. The results were shown in Table 21 below.

TABLE 21

Reconstitution results of samples with different filled volumes from batch 04 after being stored at 40° C. for 10 days

| Sample reconstitution | | |
|---|---|---|
| Sample name | Volume/ml of purified water for reconstitution | Phenomenon after reconstitution |
| 04(17 ml, 200 mg/vial) | 40 ml | very few adhesions on the vial wall |
| | 45 ml | clear solution |
| 04(13 ml, 150 mg/vial) | 30 ml | clear solution |
| | 33 ml | very few adhesions on the vial wall |
| 04(8.5 ml, 100 mg/vial) | 22 ml | clear solution |
| | 22 ml | clear solution |

Brief summary of the experiments: Storage at 40 °C for 10 days for samples from batch 04 (8.5 ml, 13 ml, and 17 ml) does not affect reconstitution. The phenomena after reconstitution for the samples do not have much difference with those for the day-0 samples.

Experimental Conclusions

Generally speaking, for containers with a fixed volume, it will be easier to reconstitute the lyophilized formulation obtained from the drug solution filleded in a smaller volume within certain range.

Regarding whether the pH value of the drug solution should be adjusted, relatively, the lyophilized formulations obtained by adjusting the pH value to about 7 have a better reconstitution performance.

By specific comparison, it can be found that the lyophilized formulations obtained with lower API concentration and lower mannitol content were easier to reconstitute. This suggested that simply increasing the API concentration and mannitol dosage to increase the drug load of the lyophilized formulation will result in difficult reconstitution. Suitable API concentration and mannitol content must be selected to obtain a lyophilized drug solution with a higher drug load that is easy for reconstitution.

7. Experiment for Investigating the Effects of pH on Sample Stability

The effects of pH on sample stability were investigated.

The drug solutions were prepared according to the scheme shown in Table 22 below. A total volume of 6500 ml was prepared. Each vial was filled with 25 mL, and 260 vials were filled in total.

TABLE 22

Preparation of drug solution for investigation of the effects of pH on sample stability

| | Drug solution | | | | |
|---|---|---|---|---|---|
| Formulation Batch No. | Prescribed amount per vial/g | Content | Batch weight/g | Actual weight/g | pH |
| API | 0.2 | 8 mg/ml | 53.78 | 52.054 | / |
| Mannitol | 1.75 | 70 mg/ml | 455 | 455.16 | |
| Tert-butanol | 5.8875 | volume ratio 30% | 1530.75 | 350.81<br>1180.39 | |
| Water | 16.6625 | volume ratio 66.65% | 4332.25 | 150.42<br>2927.55<br>1255.59 | |
| Total | 6500 ml (about 6370 g) | | | | |

Density of tert-butanol is p=0.785 g/ml, and then the mass of tert-butanol in 1950 ml is 1530.75 g. The purity of API is 99.26%.

Preparation of the Lyophilized Formulation

1. Preparation of a Solution

① Preparation of 70% tert-butanol aqueous solution: the solution was obtained by weighing 350.81 g of tert-butanol and 150.42 g of water.

② Pre-dissolution: the prescribed amount of API was weighed; API was added to 70% tert-butanol aqueous solution under stirring conditions and dissolved under stirring. The resulting solution was recorded as Solution A.

③ Under stirring conditions, the prescribed amount of mannitol was initially dissolved in 70% of the remaining water. The resulting solution was stirred until it was clear and recorded as Solution B.

④ Solutions A and B were mixed and stirred homogeneously. Then the mixed solution was added with the remaining water and remaining tert-butanol after being used to rinse; the pH of the obtained intermediate drug solution was 5.63.

⑤ The drug solution was divided into 3 equal portions.

Drug solution-01: pH was not adjusted; and the pH was measured to be 4.77 after storage at room temperature for 24 hours.

Drug solution-02: 200 μl of sodium bicarbonate was added, and the pH was measured to be 6.60 (pH between 6.0 and 6.5). The pH was measured to be 5.20 after storage at room temperature for 24 hours.

Drug solution-03: 1000 μl of sodium bicarbonate was added, and the pH was measured to be 7.20 (pH at 7.0). The pH was measured to be 6.90 after storage at room temperature for 24 hours. The intermediate drug solution at 0 hour and the drug solution after storage at room temperature for 24 hours were taken respectively, and measured for their contents and related substances.

2. Filtration

The solutions were filtered using a 250 ml sterile filter cup.

3. Filling

For Drug solution—01 batch, filled with 24.5 g to give 78 vials, and recorded as Batch 01.

For Drug solution—02 batch, filled with 24.5 g to give 78 vials, and recorded as Batch 02.

For Drug solution—03 batch, filled with 24.5 g to give 78 vials, and recorded as Batch 03.

4. Half-Stoppered

After package, the vial was half-stoppered and placed in a lyophilizer for freeze-drying.

5. Pre-Lyophilization and Lyophilization

Figure 10:
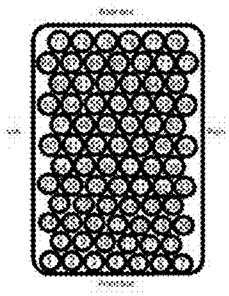
FIG. 10 shows a schematic diagram of the placement of vials on the plate of the laboratory lyophilizer.

The above-mentioned subpackaged formulations were lyophilized in a vacuum lyophilizer. The arrangement sequence of the vials in this lyophilizer model was shown in FIG. 10. The lyophilization was performed with the lyophilization parameters listed in Table 12. After lyophilization, the vials were stoppered under vacuum and crimp-capped. The lyophilized formulations were obtained. Plate temperature before discharging: 5.0 °C; the vial was manually stoppered under high vacuum.

Experimental Results

The test results of the drug solutions were shown in Table 23.

TABLE 23 pH value data of the drug solutions in different batches stored for different time periods after pH adjustment

| / | pH Value | | |
|---|---|---|---|
| Time | 1 h | 2 h | 3 h |
| Prior to pH regulation | | 5.63 | |
| 0 h after pH regulation | 5.63 | 6.60 | 7.20 |
| 24 h after pH regulation | 4.77 | 5.20 | 6.90 |

Figure 11:
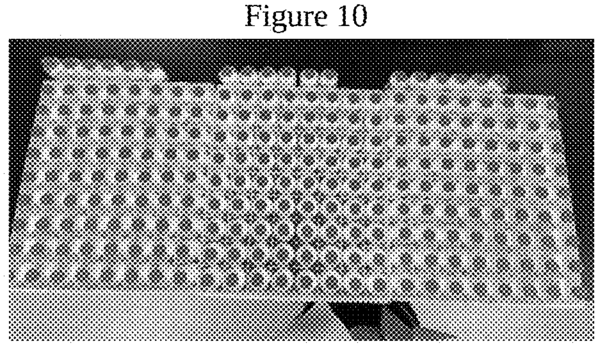
FIG. 11 shows a photograph of a lyophilized formulation sample.
Figure 12:
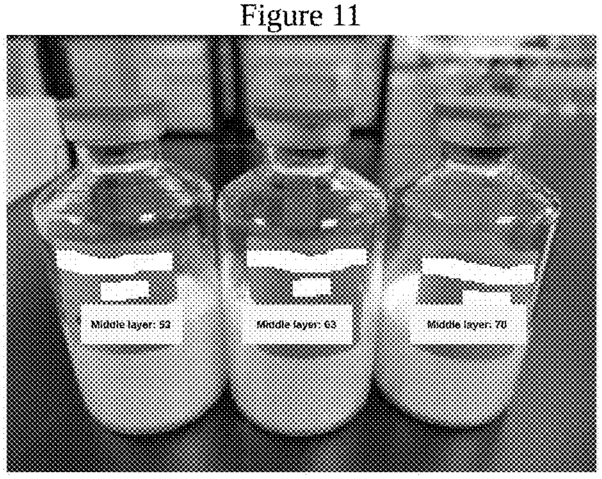
FIG. 12 shows a photograph of a sample with “neck wrapping” in a lyophilized formulation. The labels have been covered by mosaic.

The state of the lyophilized formulation sample: white cakey solid; the specific samples were shown in FIG. 11. The bottlenecks of the sample bottles from the back box in the middle of the lyophilizer were surrounded by powder, as shown in FIG. 12. It may be caused by improper operation during package.

(3) Measurement of Reconstituted Samples

Lyophilized formulations from different batches and locations were taken and reconstituted, respectively. The results were shown in Table 24 below.

TABLE 24

Reconstitution measurement data of the lyophilized formulations from different positions of the plate after lyophilization with drug solutions at different pH values from different batches

| Batch No. | Volume for reconstitution | pH | Osmotic pressure mOsmol/kg | Naked eye | Clarity test equipment (in comparison with water) |
|---|---|---|---|---|---|
| 01-upper layer No. 15 | 38 ml water | 4.45 | 267 | clear | slightly clear |
| 01-upper layer No. 11 | 38 ml water | 4.43 | 265 | clear | slightly clear |
| 01-upper layer No. 51 | 38 ml water | 4.45 | 265 | clear | slightly clear |
| 01-upper layer No. 69 | 38 ml water | 4.37 | 264 | clear | slightly clear |
| 02-middle layer No. 04 | 39 ml water | 4.64 | 264 | clear | slightly clear |
| 02-middle layer No. 15 | 38 ml water | 4.66 | 262 | clear | slightly clear |
| 02-middle layer No. 51 | 38 ml water | 4.62 | 261 | clear | slightly clear |
| 02- middle layer No. 69 | 38 ml water | 4.63 | 259 | clear | slightly clear |
| 03-lower layer No. 04 | 38 ml water | 5.94 | 263 | clear | slightly clear |
| 03-lower layer No. 06 | 38 ml water | 6.12 | 268 | clear | slightly clear |
| 03-lower layer No. 13 | 38 ml water | 5.76 | 265 | clear | slightly clear |
| 03-lower layer No. 31 | 38 ml water | 5.86 | 267 | clear | slightly clear |
| 02 - (blank powder) upper layer 23 | 38 ml water | 6.48 | 255 | clear | clear |
| 02 - (blank powder) upper layer 52 | 38 ml water | 6.33 | 252 | clear | clear |
| 02 - (blank powder) upper layer 53 | 38 ml water | 6.44 | 255 | clear | clear |
| 02 - (blank powder) upper layer 54 | 38 ml water | 6.70 | 251 | clear | clear |

Note: the reconstituted solution of batch 02 (blank powder) was as clear as water; and reconstituted solutions of batch 01, batch 02, and batch 03 were slightly more turbid than water.

In order to further investigate the reconstitution effect with the commonly used intravenous infusion solution—physiological saline, after being reconstituted with purified water to an API concentration of about 5 mg/ml, the formulation was further diluted with physiological saline to 0.5 mg/ml (5 ml was taken out to be added to 50 ml sodium chloride injection, 0.5 mg/ml): clear solutions were obtained, and then the pH value and osmotic pressure data were measured. The results were shown in Table 25 below.

TABLE 25

Reconstitution measurement data of the lyophilized formulations from located in different positions on the plate in different batches after lyophilization with drug solutions with different pH values

| Batch No. | Volume for reconstitution | pH value | pH Value after being diluted with physiological saline to 0.5 mg/ml | Osmotic pressure (0.5 mg/ml) mOsmol/kg |
|---|---|---|---|---|
| 01-upper layer No. 29 | 38 ml water | 4.53 | 5.11 | 283 |
| 01-upper layer No. 55 | 38 ml water | 4.54 | / | / |
| 01-upper layer No. 65 | 38 ml water | 4.50 | 5.07 | 284 |
| 02-middle layer No. 08 | 38 ml water | 4.60 | / | / |
| 02-middle layer No. 25 | 38 ml water | 4.63 | 5.15 | 284 |
| 02-middle layer No. 35 | 38 ml water | 4.67 | 5.18 | 284 |
| 03-lower layer No. 08 | 38 ml water | 5.90 | / | / |

TABLE 25-continued

Reconstitution measurement data of the lyophilized formulations from located in different positions on the plate in different batches after lyophilization with drug solutions with different pH values

| Batch No. | Volume for recon-stitution | pH value | pH Value after being diluted with physiological saline to 0.5 mg/ml | Osmotic pressure (0.5 mg/ml) mOsmol/kg |
|---|---|---|---|---|
| 03-lower layer No. 19 | 38 ml water | 5.78 | 5.38 | 285 |
| 03- lower layer No. 25 | 38 ml water | 5.84 | 5.25 | 285 |

Samples were taken at different time periods after reconstitution with physiological saline to measure the purity of the API by HPLC in the solution. The results were shown in Table 26 below.

TABLE 26

Purity by HPLC data of the API in the solutions reconstituted with physiological saline measured by sampling at different time periods after reconstitution from the solution with different API concentrations

| Batch No. | 0 h | 6 h | 6 h-Filtration |
|---|---|---|---|
| 5 mg/ml | | | |
| 01 | 98.98% | 98.80% | 98.82% |
| 02 | 98.94% | 98.77% | 98.77% |
| 03 | 98.80% | 98.65% | 98.66% |
| 0.5 mg/ml | | | |
| 01 | 98.95% | 98.79% | 98.80% |
| 02 | 98.91% | 98.69% | 98.69% |
| 03 | 98.80% | 98.61% | 98.61% |

(4) Solvent Residue of the Samples and Stability Testing

The lyophilized formulation samples were placed in a thermostat at 40 °C, 25 °C, and 2-8 °C, and the purities were measured by HPLC on the corresponding days. The results were shown in Table 27 below.

TABLE 27

Purity data of the lyophilized formulation samples measured by HPLC on the corresponding days after storage in the thermostat at 40° C., 25° C., and 2-8° C.

| 40° C. | | | | |
|---|---|---|---|---|
| Batch No. | Day 0 | Day 3 | Day 5 | Day 10 |
| 01 | 99.08% | 98.78% | 98.65% | 98.26% |
| 02 | 99.08% | 98.86% | 98.71% | 98.35% |
| 03 | 99.0% | 98.88% | 98.80% | 98.45% |
| 25° C. | | | | |
| Batch No. | Day 5 | Day 10 | / | / |
| 01 | 98.89% | 98.75% | / | / |
| 02 | 98.92% | 98.88% | / | / |
| 03 | 98.76% | 98.87% | / | / |

Test of the Residual Solvent

The tert-butanol (2 vials) and moisture (2 vials) contents of the 0-day samples of batch 01, batch 02, and batch 03 were measured, respectively. Note that samples from the middle of the freeze-drying machine plate were taken. The results are shown in Table 28 below.

TABLE 28

Residual solvent content of lyophilized formulations prepared from three batches of drug solutions with different pH values

| Batch No. | Water content (percent by mass) | Tert-butanol content (percent by mass) |
|---|---|---|
| 01 | 5.19% | 0.75% |
| 02 | 5.10% | 0.70% |
| 03 | 5.03% | 0.80% |

8. Preparation Examples of Formulation Lyophilized with the Solutions with Different Tert-Butanol Concentrations, Different Excipients (Sucrose or Mannitol), Different Excipient Amounts, Different Drug Contents, and Different pH Values after Lyophilization Considering that the quality indicators of lyophilized formulations include three main investigative indicators: reconstitution, stability, and residual solvent, and it can be found from the above experiments that the influencing factors include solvent (volume ratio of tert-butanol in the tert-butanol-water mixed solvent), API concentration, type (mannitol or sucrose) and amount of excipients, and pH value of the drug solution, the inventors have conducted several multi-factor experiments. The results were shown in Table 28 below.

TABLE 28

Data of lyophilized formulations prepared from drug solutions with different volume ratios of tert-butanol, API concentrations, types and amounts of excipients, and pH values of the drug solutions in the examples

| Batch No. | Deliverable Volume | Formulation | Purity by HPLC after placement at 40° C. on different days (%) 0 | 3 | 5 | 10 | 15 | 20 | 30 | Residual Solvent water % | TBA % |
|---|---|---|---|---|---|---|---|---|---|---|---|
| F00610602 | 25 | 30% TBA/70Mannitol/8.5API-pH 7.0 | 96.62 | 92.60 | / | / | / | / | / | / | / |
| F00610603 | 25 | | 96.69 | 94.74 | / | / | / | / | / | / | / |
| F00609801 | 25 | 30% TBA/70Mannitol/8API-pH 7.0 | 96.66 | 93.74 | / | 94.53 | / | / | / | / | / |
| F00609802 | | | 96.66 | 91.03 | / | 79.79 | / | / | / | / | / |
| F006088 | 25 | 30% TBA/70Mannitol/8API-pH 7.0 | 96.86 | / | 89.91 | 93.28 | / | / | / | / | / |
| F00608001 | 10 | 30% TBA/70Mannitol/8.5API-pH 7.0 | 96.11 | / | / | 72.99 | / | / | / | / | 0.57 |
| F00608002 | 25 | | 96.17 | / | / | 87.85 | / | / | / | / | 0.41 |
| F00608003 | 25 | | 96.18 | / | / | 94.20 | / | / | / | / | 0.37 |
| F00608004 | 25 | | 96.12 | / | / | 94.57 | / | / | / | / | 0.39 |

TABLE 28-continued

Data of lyophilized formulations prepared from drug solutions with different volume ratios of tert-butanol, API concentrations, types and amounts of excipients, and pH values of the drug solutions in the examples

| Batch No. | Deliverable Volume | Formulation | Purity by HPLC after placement at 40° C. on different days (%) 0 | 3 | 5 | 10 | 15 | 20 | 30 | Residual Solvent water % | TBA % |
|---|---|---|---|---|---|---|---|---|---|---|---|
| F00607001 | 10 | 30% TBA/70Mannitol/8.5API-pH 7.0 | 96.55 | / | / | 71.99 | / | / | / | / | 0.42 |
| F00607002 | 25 | | 97.04 | / | / | 85.80 | / | / | / | / | 0.39 |
| F00607003 | 10 | | 96.04 | / | / | 70.68 | / | / | / | / | 0.43 |
| F00607004 | 25 | | 96.70 | / | / | 82.45 | / | / | / | / | 0.37 |
| F00606001 | 10 | 30% TBA/70Mannitol/8.5API-pH 7.0 | 95.97 | 88.58 | 82.11 | 70.89 | / | / | / | / | 0.35 |
| F00606002 | 25 | | 96.67 | 88.01 | 81.49 | 66.31 | / | / | / | / | 0.29 |
| F00606003 | 10 | | 95.52 | 86.70 | 80.17 | 65.12 | / | / | / | / | 0.30 |
| F00606004 | 25 | | 96.47 | 87.03 | 79.86 | 64.20 | / | / | / | / | 0.27 |
| F00605201 | 10 | 30% TBA/70Mannitol/8.5API-pH 7.0 | 97.51 | 90.87 | 87.69 | 87.63 | / | / | 80.84 | 0.49 | 0.60 |
| F00605202 | 25 | | 97.95 | 97.67 | 96.85 | 96.48 | / | / | 94.88 | 1.55 | 0.70 |
| F00605203 | 28 | | 98.18 | 97.84 | 96.81 | 96.81 | / | / | 95.52 | 1.60 | 0.59 |
| F00604601 | 25 | 30% TBA/70Mannitol/8.5API-pH 7.0 | 97.32 | 97.57 | 97.54 | 97.04 | / | / | 95.98 | 0.55 | 0.52 |
| F00604602 | 28 | | 97.26 | 97.16 | 97.54 | 97.22 | / | / | 96.59 | 1.62 | / |
| F00604603 | 25 | | 98.19 | 95.90 | 97.65 | 95.66 | / | / | 96.40 | 2.06 | 1.11 |
| F00604604 | 28 | | 97.88 | 97.88 | 97.75 | 85.16 | / | / | 94.53 | 1.86 | 4.73 |
| F00604001 | 14 | 60% TBA/90Sucrose/15API | 98.67 | 91.52 | / | / | 62.68 | 54.26 | 36.49 | / | / |
| F00604002 | 14 | 60% TBA/90Sucrose/15API-pH 7.0 | 98.57 | 91.46 | / | / | 62.31 | 54.51 | 35.85 | / | / |
| F00604003 | 25 | 30% TBA/70Mannitol/8.5API-pH 7.0 | 97.98 | 97.42 | / | / | 96.79 | 96.54 | 96.29 | / | / |
| F00603301 | 21 | 30% TBA/70Mannitol/10API-pH 7.0 | 97.39 | 97.11 | 97.11 | / | | 96.65 | 95.62 | 1.52 | 0.61 |
| F00602501 | 11 | 30% TBA/70Mannitol/10API-pH 7.0 | 96.78 | / | 90.54 | 89.40 | / | / | / | / | / |
| F00602502 | 16 | | 97.11 | / | 95.26 | 94.47 | / | / | / | / | / |
| F00602503 | 19 | | 97.09 | / | 96.62 | 96.34 | / | / | / | / | / |
| F00602504 | 21 | | 96.99 | / | 96.42 | 96.92 | / | / | / | / | / |
| F00601201 | 10.5 | 40% TBA/60Mannitol/10API | 97.34 | / | 91.96 | / | / | 85.43 | / | / | / |
| | 16 | | 97.37 | / | 94.78 | / | / | 90.51 | / | / | / |
| | 21 | | 97.25 | / | / | / | / | 96.28 | / | / | / |
| F00601202 | 10.5 | 40% TBA/60Mannitol/10API-pH 7.0 | 97.00 | / | 92.33 | / | / | 84.64 | / | / | / |
| | 16 | | 96.68 | / | / | / | / | 92.37 | / | / | / |
| | 21 | | 97.34 | / | / | / | / | 95.74 | / | / | / |
| F00601203 | 10.5 | 30% TBA/70Mannitol/12.5API | 97.14 | / | / | / | / | 88.46 | / | / | / |
| | 16 | | 97.59 | / | / | / | / | 86.89 | / | | / |
| | 21 | | 97.58 | / | / | / | / | 87.97 | / | / | / |
| F00601204 | 10.5 | 30% TBA/70Mannitol/12.5API-pH 7.0 | 97.21 | / | / | / | / | 90.92 | / | / | / |
| | 16 | | 97.44 | / | / | / | / | 88.64 | / | / | / |
| | 21 | | 97.40 | / | / | / | / | 89.34 | / | / | / |
| F00600101 | 10 | 40% TBA/80Mannitol/10API | 96.41 | / | 88.32 | / | / | 76.88 | / | / | / |
| F00600102 | 10 | 40% TBA/80Mannitol/10API-pH 7.0 | 96.19 | / | / | / | / | 82.88 | / | / | / |
| F00600103 | 10.5 | 40% TBA/80Mannitol/20API | 97.23 | / | 93.89 | / | / | 89.82 | / | / | / |
| F00600103 | lyophilized tray | 40% TBA/80Mannitol/20API | 98.00 | / | / | 97.56 | 97.10 | | 96.29 | / | / |
| F00714901 | 14 | 40% TBA/80Mannitol/15API | 97.45 | 93.62 | 93.73 | / | / | 88.15 | / | / | / |
| F00714902 | 10.5 | 40% TBA/80Mannitol/20API | 97.53 | 95.14 | 94.55 | / | / | 91.27 | / | / | / |
| F00714903 | 14 | 40% TBA/80Mannitol/15API-pH 7.0 | 97.51 | / | 94.18 | / | / | 90.87 | / | / | / |
| F00714904 | 10.5 | 40% TBA/80Mannitol/20API-pH 7.0 | 97.67 | 95.38 | 95.17 | / | / | 95.84 | / | / | / |
| F00714905 | 12 | 60% TBA/100Sucrose/25API | 98.31 | 89.12 | 86.77 | / | / | 74.95 | / | / | / |
| F00714905 | lyophilized tray | 40% TBA/100Sucrose/25API | 97.60 | / | / | / | / | 97.12 | 96.22 | | |
| F00713001 | 10.5 | 40% TBA/80Mannitol/20API | 97.91 | 95.15 | 94.05 | 90.56 | / | / | / | / | / |
| F00713002 | | 40% TBA/80Mannitol/20API-pH 5 | 97.97 | 95.20 | 94.17 | 90.61 | | / | / | / | / |
| F00713003 | | 40% TBA/80Mannitol/20API-pH 6 | 98.03 | 95.02 | 94.29 | 90.23 | / | / | / | / | / |
| F00713004 | 10.5 | 40% TBA/80Mannitol/20API-pH 7 | 98.05 | 95.31 | 94.14 | 91.14 | / | / | / | / | / |
| F00713005 | | 40% TBA/80Mannitol/20API-pH 8 | 97.85 | 94.95 | 93.76 | 90.84 | / | / | / | / | / |
| F00713006 | | 40% TBA/60Mannitol/20API-pH 6 | 98.41 | 96.40 | 95.60 | 92.69 | / | / | / | / | / |
| F00713007 | | 40% TBA/70Mannitol/20API-pH 6 | 98.18 | 95.63 | 94.69 | 92.10 | / | / | / | / | / |
| F00713008 | | 40% TBA/100Mannitol/20API-pH 6 | 98.43 | 95.68 | 94.53 | 91.11 | / | / | / | / | / |
| F00713009 | | 40% TBA/80Mannitol/20API-PBS | 97.75 | 95.19 | 94.25 | 92.89 | / | / | / | / | / |
| F00713010 | | 40% TBA/80Mannitol/15API-PBS | 97.40 | 94.38 | 93.53 | 89.75 | / | / | / | / | / |
| F00712501 | 10.5 | 40% TBA/80Mannitol/20API-pH 7 | 97.67 | 95.30 | 94.24 | 92.52 | / | / | / | / | / |
| F00711801 | 16.5 | 40% TBA/80Mannitol/20API-pH 7 | 97.47 | 95.11 | 94.09 | 93.80 | / | / | / | / | / |
| F00711401 | 1 | 40% TBA/100Sucrose/25API-pH 7 | 98.51 | 90.91 | 83.91 | 71.04 | / | / | / | / | / |
| F00711402 | | 40% TBA/80Mannitol/20API-pH 7 | 97.82 | 93.92 | 93.06 | 91.66 | / | / | / | / | / |
| F00710601 | | 40% TBA/100Sucrose/25API | 98.01 | 88.89 | 84.37 | 69.58 | / | / | / | / | / |
| F00710602 | 1 | 40% TBA/80Mannitol/20API | 97.01 | 96.03 | 96.56 | 94.85 | / | / | / | / | / |
| F00710603 | | 60% TBA/100Sucrose/25API | 98.40 | 89.18 | 84.60 | 69.82 | / | / | / | / | / |
| F00710604 | | 60% TBA/40Mannitol/20API | 98.29 | 95.89 | 95.33 | 93.99 | / | / | / | / | / |
| F00710605 | | 100Sucrose/5API | 95.68 | 84.65 | 80.15 | 67.06 | / | / | / | / | / |

Note:
TBA is tert-butanol.
Mannitol is mannitol.
Sucrose is sucrose.
API is the active pharmaceutical ingredient TH-302.
PBS is Phosphate Buffered Physiological Saline, with a pH value stable at about 7.4.

"30% TBA/70Mannitol/10API-pH7.0" in the formulation means 30% volume ratio of tert-butanol, 70 mg/ml of mannitol, 10 mg/ml of API, and 7.0 of pH adjusted by adding $NaHCO_3$. The preparation method was the same as those mentioned in the above examples. "40% TBA/60Mannitol/10API" means 40% volume ratio of tert-butanol, 60 mg/ml of mannitol, 10 mg/ml of API, without pH adjustment (weak acidity), and so on for the rest.

50 ml vials were used except for 5 ml vials used for the batch with a deliverable volume of 1 ml.

Experimental Conclusions

1. From the solubility data of TH-302 in the tert-butanol-water mixed solvent system in combination with the above-mentioned experiments and the 85 groups of exploratory experimental results shown in Table 28 above, it can be estimated or validated that the compound can be stably present in the solution when its content is ranging from 5-500 mg/ml; and the experiments have demonstrated that lyophilization is possible when the content is greater than 8 mg/ml and less than or equal to 200 mg/ml, though the lyophilizing parameters may need to be adjusted, e.g., being pre-lyophilized at −80 °C, being lyophilized at much lower absolute air pressure, longer drying duration, and lower drying temperature. Preferably, when the content of the compound of formula I in the solution is greater than or equal to 8 mg/ml and less than or equal to 25 mg/ml, the lyophilized formulation has better stability and is easier to reconstitute. The content of the compound of formula I in the solution is greater than or equal to 8 mg/ml and less than or equal to 15 mg/ml. Such a content range means relatively mild lyophilizing conditions and shorter lyophilizing cycle. The content of the compound of formula I in the solution being greater than or equal to 8 mg/ml and less than or equal to 10 mg/ml furthers means that the lyophilized formulation has commercial large-scale production value under commercially suitable lyophilization cycles and low-temperature conditions: unsuitable API content may lead to broken vials or spraying powders in the large-scale lyophilizer used during commercial mass production due to uneven heating temperatures, thereby resulting in a yield lower than 90% of the acceptance level for commercial production.

2. From the solubility data of TH-302 in the tert-butanol-water mixed solvent system in combination with the above experiments and the results of the 85 groups of exploratory experiments shown in Table 28 above, it can be estimated or validated that when the volume percentage of tert-butanol relative to the solution is 1-99% or the content of tert-butanol in the solution is 7.85-777.15 mg/ml (under the condition that the density of tert-butanol is 0.785 g/ml), the prepared TH-302 solution is stable and clear, and the experiments have demonstrated that lyophilization is possible when the volume ratio is 5-95% or the tert-butanol content in the solution is 39.25-745.75 mg/ml (under the condition that the tert-butanol density is 0.785 g/ml), though the lyophilizing parameters may need to be adjusted, e.g., pre-lyophilizing at −80 °C, lower absolute air pressure during lyophilization, longer drying duration and lower drying temperature. Preferably, when the volume ratio of tert-butanol is 30-60% or the tert-butanol content in the solution is 235.5-471 mg/ml (under the condition that the tert-butanol density is 0.785 g/ml), the lyophilized formulation has better stability and are easier to be reconstituted.

In fact, in the tert-butanol-water mixed solvent system, excessively higher tert-butanol content will affect the subsequent dissolution of mannitol/sucrose, and after mannitol/sucrose has served as the excipient, their amounts will directly affect the quality of the subsequent lyophilized formulation: if the amount of mannitol/sucrose is too low, the drug solution will be unable to be evenly loaded onto the excipient skeletons after lyophilization, or even cause collapse of the lyophilized powder cake or failure of lyophilization during the drying stage of the lyophilizing process. Thus, the content of tert-butanol cannot be increased inappropriately merely for the purpose of increasing the solubility of TH-302.

3. According to the solubility data of TH-302 in the tert-butanol-water mixed solvent system in combination with the above experiments and the results of the 85 groups of exploratory experiments shown in Table 28 above, it can be seen that the lyophilized formulations can be obtained when mannitol, PEG2000, P188, SBECD, DSPE-MPEG2000, sucrose or other similar substances is used as the excipient. However, after comparison, it is more appropriate to use sucrose and mannitol after comprehensively considering the factors besides those of the lyophilized formulation itself, e.g., whether it could be routinely used and commercially available, and whether it will affect the efficacy, DMPK and toxicology. The lyophilized formulations prepared by using such an excipient have appropriate stability in solution (a duration of at least 24 hours at room temperature), and the lyophilized formulations are stable, could be readily reconstituted, and are easy to obtain products that meet the requirements of excipients for injection formulations.

4. In fact, just as mentioned under the above Item 2, a higher content of mannitol/sucrose as an excipient does not necessarily mean a better effect: although a higher amount of the excipient can provide lyophilized skeletons loading more drugs and is also beneficial for lyophilization production and improving the stability of lyophilized formulations, it is affected by its solubility in the tert-butanol-water mixed solvent system. Excessively higher amount of mannitol/sucrose may make the mixed solvent unable to be completely dissolved or the solution unstable, and thus precipitation may occur during the pre-lyophilizing stage or cooling stage. Thus, the amount of mannitol/sucrose used as an excipient in the lyophilized solution should also be within a suitable range to meet the above-mentioned requirements.

The content of sucrose or mannitol in the solution is 20-300 mg/ml. Such a range can meet the above requirements: the drug solution is stable and precipitation is not easy to occur during the pre-lyophilizing stage or cooling stage of the lyophilization process. Further preferably, the content is 40-100 mg/ml, and it is possible to obtain a reconstituted solution and a lyophilized formulation with good stability. More preferably, the content is 60-70 mg/ml. Such a content range means that the lyophilizing conditions are relatively mild and the lyophilizing cycle is in line with commercial production practices (less than 10 days, i.e., a 240-hour for one production cycle).

5. As mentioned in the above Item 2, excessively low amount of mannitol/sucrose will cause the drug solution to be unable to be evenly loaded on the excipient skeletons after lyophilization, or may even cause the lyophilized powder cake to collapse during the drying stage of the lyophilization process or failure of lyophilization; and although excessively high amount of mannitol/sucrose can produce a lyophilized formulation with better appearance and stability, it means that the content of the drug TH-302 in the lyophilized formulation per unit package would be too low to meet the requirements for commercial sales and usage. Thus, a suitable ratio between mannitol/sucrose and the active drug is essential. The mass ratio of the compound of formula I to the excipient in the solution is in the range of 1: (0.5-20). Such a ratio can meet the requirements as mentioned in the above Items 1-4 for the other ingredients, and can enable the prepared lyophilized formulation to have better appearance and stability; preferably the mass ratio is in the range of 1:(2-12.5), which can afford a better lyophilized formulation that is easy to reconstitute; and more preferably the mass ratio is in the range of 1:(5-10), with which the prepared lyophilized formulation will have excellent properties: having good stability of lyophilized formulations, being easy to reconstitute, having mild lyophilizing conditions and short lyophilizing cycle.

6. Experimental phenomena showed that the pH value of the drug solution for lyophilization will directly affect its stability and the complexity level of reconstitution and the stability of the corresponding lyophilized formulation. Experiments have proved that if the drug solution was not added with a pH regulator (a base or basic salt), the drug solution would be acidic, and the acidic drug solution would have poor stability, the corresponding lyophilized formulation would be reconstituted unsatisfactorily and have low stability; when a pH regulator (a base or basic salt) was added, these could be improved significantly.

7. It is worth mentioning that the filled volume of the drug solution in the vial can also affect the appearance and reconstitution of the finally lyophilized powder cake (powder being sprayed or adhered to the bottleneck of the vial) by multiple factors. Therefore, the ratio of the filled volume of the drug solution in the vial and the volume of the vial must be appropriate. After considering the above-mentioned experimental data and the actual production practice, it is appropriate that the filled volume of the lyophilized drug solution is ⅓ to ½ of the volume of the sealed container, and the volume of the corresponding lyophilized formulation is ⅓ to ½ of the volume of the sealed container.

9. Saturated Solubility of the Drug in D5W Solution (Under Strong Shaking Conditions)

The TH-302 sample was weighed accurately in an amount of about 60 mg, placed in a transparent vial, and added with 6 ml of dextrose 5% in water (D5W). The resulting solution was shaked vigorously for 2 minutes to obtain a solubility-stock solution. It was observed that the solubility-stock solution contained insoluble substances. Thus, the solubility-preserving solution was filtered and then became clear. The filtered filtrate was left to stand at room temperature for 24 hours, and was found to be still clear. After sampling and appropriate dilution, the content of the solution was measured by HPLC to be 7.25 mg/ml. This value was exactly the saturated solubility of the drug in D5W solution.

It can thus be seen that the concentration of TH-302 in the TH-302-containing injection for intravenous administration should be within the range of 0-7.25 mg/ml. In fact, considering the isotonicity and the osmotic pressure of the glucose contained in intravenous injection, further research is needed to determine suitable infusion formula during intravenous drip.

10. Statistical Results of Height Measurement of the Drug Solution Pre- and Post-Lyophilization in 50 ml Vials (Calculation of Drug Load and Drug Mass Percentage)

The drug solution in Experiment 7 was filled: 25 ml of the drug solution was filled into a 50 ml vial, and the liquid level height after the drug solution being filled was measured. The average height was 26.5 mm. After lyophilization, the heights of the lyophilized powder cake in the vials at different plate positions of the lyophilizer were measured, and the difference in volume compared with the 25 ml before filling was roughly calculated.

In the multi-batch experiments, it was found that the volumes before lyophilization in some batches were increased after lyophilization, in some batches were decreased, and in some batches remained almost unchanged. By marking the liquid levels before and after lyophilization and statistically analyzing the volume changes, it was found that the maximum amplitude of volume increment or decrease is 10%; that is, the volume change is within +10%.

In the case where the volume of the lyophilized powder cake is decreased by 10% after lyophilization:

when the API content of the drug solution is greater than or equal to 5 mg/ml and less than or equal to 500 mg/ml, the drug load of the lyophilized powder cake after lyophilization is 5/0.9 to 500/0.9, i.e., 5.55-555.55 mg/$cm^3$; and it was calculated by the same method that:

when the content of the compound of formula I in the drug solution is in the range of 5-160 mg/ml, the drug load of the lyophilized powder cake is 5.55-177.77 mg/$cm^3$;

when the content of the compound of formula I in the drug solution is in the range of 8-50 mg/ml, the drug load of the lyophilized powder cake is 8.88-55.55 mg/$cm^3$;

when the content of the compound of formula I in the drug solution is in the range of 8-25 mg/ml, the drug load of the lyophilized powder cake is 8.88-27.77 mg/$cm^3$;

when the content of the compound of formula I in the drug solution is in the range of 8-15 mg/ml, the drug load of the lyophilized powder cake is 8.88-16.66 mg/$cm^3$;

when the content of the compound of formula I in the drug solution is in the range of 8-10 mg/ml, the drug load of the lyophilized powder cake is 8.88-11.11 mg/$cm^3$.

If the content of the drug solution is 6, 7, 7.5, 8, 8.5, 10, 12.5, 15, 20, or 25 mg/ml, the corresponding drug load of the lyophilized powder cake is 6.66, 7.77, 8.33, 8.88, 9.44, 11.11, 13.88, 16.66, 22.22, or 27.77 mg/$cm^3$.

In the case where the volume of the lyophilized powder cake is increased by 10% after lyophilization:

when the API content of the drug solution is greater than or equal to 5 mg/ml and less than or equal to 500 mg/ml, the drug load of the lyophilized powder cake after lyophilization is 5/1.1 to 500/1.1, i.e., 4.55-454.55 mg/$cm^3$; and it was calculated by the same method that:

when the content of the compound of formula I in the drug solution is in the range of 5-160 mg/ml, the drug load of the lyophilized powder cake is 4.55-145.45 mg/$cm^3$;

when the content of the compound of formula I in the drug solution is in the range of 8-50 mg/ml, the drug load of the lyophilized powder cake is 7.27-45.45 mg/$cm^3$;

when the content of the compound of formula I in the drug solution is in the range of 8-25 mg/ml, the drug load of the lyophilized powder cake is 7.27-22.73 mg/$cm^3$;

when the content of the compound of formula I in the drug solution is in the range of 8-15 mg/ml, the drug load of the lyophilized powder cake is 7.27-13.64 mg/$cm^3$; and when the content of the compound of formula I in the drug solution is in the range of 8-10 mg/ml, the drug load of the lyophilized powder cake is 7.27-9.09 mg/$cm^3$.

If the content of the drug solution is 6, 7, 7.5, 8, 8.5, 10, 12.5, 15, 20, or 25 mg/ml, the corresponding drug load of the lyophilized powder cake is 5.45, 6.36, 6.82, 7.27, 7.73, 9.09, 11.36, 13.64, 18.18, or 22.73 mg/$cm^3$.

Since the formulation obtained by lyophilizing drug solution contains API drug, excipients, and residual tert-butanol solvent and water, and the mass ratio of the API drugs and excipients in the lyophilized formulations prepared by the applicants is in the range of 1: (0.5-20), the maximum allowable tert-butanol content is 1.75% by mass, and the water content is 6% by mass, then the lower limit of the API drugs by mass percentage in the lyophilized formulation is (1/20+1)*(1-6%-1.75%)=4.76%*92.25%=4.39%, and the upper limit is (1/0.5+1)*(1-0%-0%)=66.66%; that is, the content of the API drug in the lyophilized formulation is greater than or equal to 4.39% and less than 66.66%.

The invention claimed is:

1. A solution comprising a compound of the following formula I, water and tert-butanol, (I)

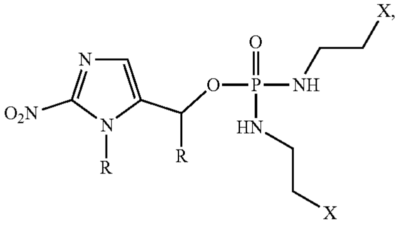

wherein R is each independently selected from H, —$CH_3$, and —$CH_2CH_3$; and X is each independently selected from Br, Cl, OMs, and OTs, water and tert-butanol are used as a mixed solvent, and the content of the compound of formula I in the solution is greater than or equal to 1 mg/ml and less than or equal to 500 mg/ml.

2. The solution according to claim 1, wherein the solution is used for preparing a lyophilized formulation with a high drug load, and further comprises an excipient, wherein the content of the compound of formula I in the solution is greater than or equal to 5 mg/ml and less than or equal to 500 mg/ml, wherein the excipient is selected from sucrose and mannitol; the content of sucrose or mannitol in the solution is in the range of 20-300 mg/ml; and the mass ratio of the compound of formula I and the excipient in the solution is in the range of 1: (0.5-20).

3. The solution according to claim 1, wherein the compound of formula I is selected from the group consisting of (I-1)

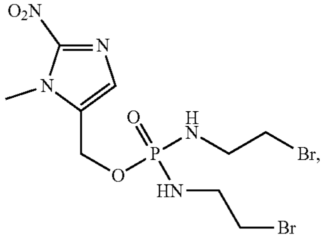

(I-2-)

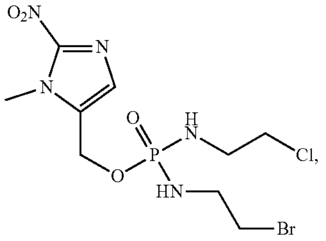

and

-continued (I-3)

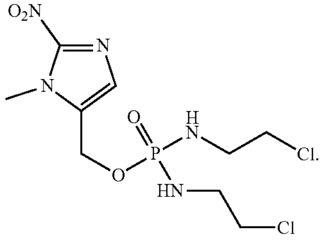

4. The solution according to claim 1, wherein the content of the compound of formula I in the solution is greater than or equal to 5 mg/ml and less than or equal to 160 mg/ml.

5. The solution according to claim 1, wherein the volume percentage of tert-butanol relative to the solution is in the range of 1-99%; or the content of tert-butanol in the solution is in the range of 7.85-777.15 mg/ml.

6. The solution according to claim 1, further comprising a pH regulator selected from hydrochloric acid, sodium hydroxide, triethanolamine, citric acid, phosphoric acid, lactic acid, tartaric acid, succinic acid, sodium bicarbonate, sodium carbonate, or a mixture thereof.

7. The solution according to claim 1, wherein the solution is used for preparing a lyophilized formulation with a high drug load, consisting of a compound of the following formula I-1, water, tert-butanol, sucrose, and sodium bicarbonate; or a compound of the following formula I-1, water, tert-butanol, mannitol, and sodium bicarbonate;

(I-1)

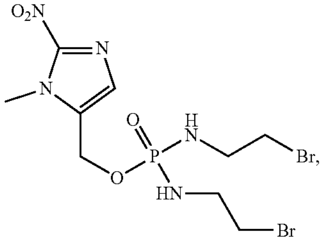

water and tert-butanol are used as a mixed solvent;

the volume content of tert-butanol relative to the solution is 30%, 40%, or 60%, or the content of tert-butanol in the solution is 235.5, 314, or 471 mg/ml;

the content of the compound of formula I-1 in the solution is 6, 7, 7.5, 8, 8.5, 10, 12.5, 15, 20, or 25 mg/ml;

sucrose or mannitol is used as an excipient, and the content of sucrose or mannitol in the solution is 40, 50, 60, 70, 75, 80, 90, or 100 mg/ml;

the content of the sodium bicarbonate is such that the pH value of the solution is in the range of 4-9, and wherein the mass ratio of compound I-1 to sucrose or mannitol in the solution is 1:2, 1:3, 1:3.5, 1:4, 1:5, 1:5.333, 1:5.6, 1:6, 1:1.67, 1:7, 1:8, 1:8.235, 1:8.75, or 1:9.375.

8. A lyophilized formulation, comprising a compound of the following formula I, an excipient, residual solvent components, and optionally a pH regulator, (I)

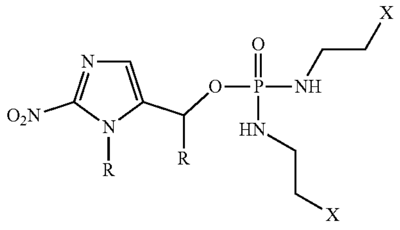

wherein R is each independently selected from H, —$CH_3$, and —$CH_2CH_3$; and X is each independently selected from Br, Cl, OMs, and OTs;

the drug load of the compound of formula I in the lyophilized formulation is greater than 5.55 mg/$cm^3$ and less than or equal to 177.77 mg/$cm^3$;

the residual solvent components are water and tert-butanol; and the pH regulator is sodium bicarbonate, and its content is in the range of 0.01-0.10 mg/$cm^3$.

9. The lyophilized formulation according to claim 8, wherein the compound of formula I is selected from (I-1)

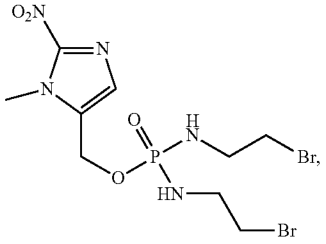

(I-2)

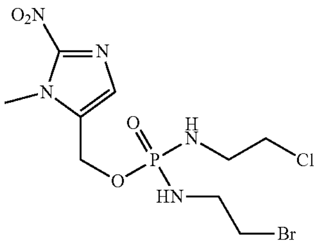

and (I-3)

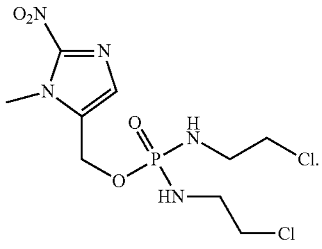

10. The lyophilized formulation according to claim 8, wherein the excipient is saccharide, polyol, polyvinylpyrrolidone, protein, poloxamer or a combination thereof;

the saccharide is selected from sucrose, dextran, cyclodextrin, maltodextrin, trehalose, lactose, maltose, and glucose;

the polyol is selected from the group consisting of glycerin, sorbitol, mannitol, inositol, ethylene glycol, polyethylene glycol, polysorbate, and adonitol;

the protein is albumin; and the poloxamer is selected from poloxamer 182, poloxamer 184, poloxamer 188, and poloxamer 407.

11. The lyophilized formulation according to claim 8, wherein the residual water content is less than or equal to 6% by mass; and the residual tert-butanol content is less than or equal to 1.75% by mass.

12. The lyophilized formulation according to claim 8, wherein the mass ratio of the compound of formula I and the excipient is 1: (0.5-20).

13. The lyophilized formulation according to claim 8, wherein the drug load of the compound of formula I in the lyophilized formulation is greater than or equal to 8.88 mg/$cm^3$ and less than or equal to 177.77 mg/$cm^3$.

14. The lyophilized formulation according to claim 8, essentially consisting of the following compound I-1, an excipient, residual water, residual tert-butanol, and optionally a pH regulator, (I-1)

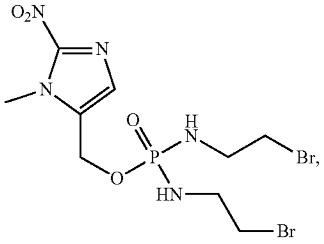

wherein the drug load of the compound of formula I-1 in the lyophilized formulation is 5.55-27.77 mg/$cm^3$;

the excipient is sucrose or mannitol;

the mass ratio of the compound of formula I-1 to the excipient is 1:2-1:9.375;

the residual water content is less than or equal to 6% by mass; and the residual tert-butanol content is less than or equal to 1.75% by mass; and the pH regulator is sodium bicarbonate, and its content is in the range of 0.01-0.10 mg/$cm^3$.

15. A unit package containing the lyophilized formulation according to claim 8, which has the following characteristics:

the lyophilized formulation is contained in a sealed container with a capacity of 100 ml; the volume of the lyophilized formulation is from ⅕ to ⅔ of the volume of the sealed container, and the amount of the compound of formula I is in the range of 400-2000 mg; or the lyophilized formulation is contained in a sealed container with a capacity of 50 ml; the volume of the lyophilized formulation is from ⅕ to ⅔ of the volume of the sealed container, and the amount of the compound of formula I is in the range of 50-800 mg; or the lyophilized formulation is contained in a sealed container with a capacity of 30 ml; the volume of the lyophilized formulation is from ⅕ to ⅔ of the volume of the sealed container, and the content of the compound of formula I is in the range of 150-600 mg; or the lyophilized formulation is contained in a sealed container with a capacity of 25 ml; the volume of the lyophilized formulation is from ⅕ to ⅔ of the volume of the sealed container, and the amount of the compound of formula I is in the range 125-500 mg; or the lyophilized formulation is contained in a sealed container with a capacity of 20 ml; the volume of the lyophilized formulation is from ⅕ to ⅔ of the volume of the sealed container, and the amount of the compound of formula I is in the range of 100-400 mg; or the lyophilized formulation is contained in a sealed container with a capacity of 18 ml; the volume of the lyophilized formulation is from ⅕ to ⅔ of the volume of the sealed container, and the amount of the compound of formula I is in the range of 90-360 mg; or the lyophilized formulation is contained in a sealed container with a capacity of 15 ml; the volume of the lyophilized formulation is from ⅕ to ⅔ of the volume of the sealed container, and the amount of the compound of formula I is in the range of 75-300 mg; or the lyophilized formulation is contained in a sealed container with a capacity of 10 ml; the volume of the lyophilized formulation is from ⅕ to ⅔ of the volume of the sealed container, and the amount of the compound of formula I is in the range of 50-200 mg; or the lyophilized formulation is contained in a sealed container with a capacity of 8 ml; the volume of the lyophilized formulation is from ⅕ to ⅔ of the volume of the sealed container, and the amount of the compound of formula I is in the range of 40-160 mg; or the lyophilized formulation is contained in a sealed container with a capacity of 7 ml; the volume of the lyophilized formulation is from ⅕ to ⅔ of the volume of the sealed container, and the amount of the compound of formula I is in the range of 35-140 mg; or the lyophilized formulation is contained in a sealed container with a capacity of 5 ml; the volume of the lyophilized formulation is from ⅕ to ⅔ of the volume of the sealed container, and the amount of the compound of formula I is in the range of 25-100 mg.

16. An injection for intravenous injection containing TH-302, wherein the solvent is water; the solute comprises the active pharmaceutical ingredient TH-302, an isoosmotic adjusting reagent; mannitol or sucrose; tert-butanol; and sodium bicarbonate, and the isoosmotic adjusting reagent is selected from glucose and sodium chloride.

17. A method for preparing a solution of the lyophilized formulation with a high drug load, comprising the following procedures:

Procedure 1: the prescribed amount of the active pharmaceutical ingredient TH-302 was weighed, added into an aqueous tert-butanol solution, and stirred until it was clear to obtain a first solution;

Procedure 2: the prescribed amount of mannitol or sucrose was dissolved in an appropriate amount of water, stirred until it was clear to obtain a second solution;

Procedure 3: the first solution and the second solution were mixed, and finally added with the remaining prescribed amount of tert-butanol, and then added an appropriate amount of water to the predetermined volume, and further added the prescribed amount of sodium bicarbonate, and mixed homogenously under stirring;

wherein the content of the active pharmaceutical ingredient TH-302 in the solution of the lyophilized formulation with a high drug loading is greater than 5 mg/ml and less than or equal to 500 mg/ml;

the volume percentage of tert-butanol relative to the solution of the lyophilized formulation with a high drug load is in the range of 1-99%, or the content of tert-butanol in the solution is in the range of 7.85-777.15 mg/ml;

the content of sucrose or mannitol in the solution of the lyophilized formulation with a high drug load is in the range of 20-300 mg/ml;

the mass ratio of TH-302 to sucrose or mannitol in the solution of the lyophilized formulation with a high drug load is in the range of 1: (0.5-20);

the volume ratio of tert-butanol in the aqueous tert-butanol solution is in the range of 30-90%; and the content of sodium bicarbonate in the solution of the lyophilized formulation with a high drug load is in the range of 0.01-0.10 mg/ml.

18. A method for preparing the lyophilized formulation with a high drug load, comprising the following procedures:

pre-lyophilization: an appropriate amount of the solution according to claim 1 is placed in a lyophilizing system and pre-lyophilized; the pre-lyophilization process comprises holding the temperature at 0 °C for a period of time and holding the temperature at −20 to −55 °C for a period of time;

primary drying: the temperature is elevated to −10 to 10 °C after pre-lyophilization and holding that temperature for a period of time, and the drying is performed by maintaining a vacuum; and secondary drying: the temperature is elevated to 20 to 40 °C after the primary drying and holding that temperature for a period of time, and the drying is performed by maintaining a vacuum.

19. The solution according to claim 1, comprising a compound of the following formula I-1, water and tert-butanol, an excipient, and optionally a pH regulator, (I-1)

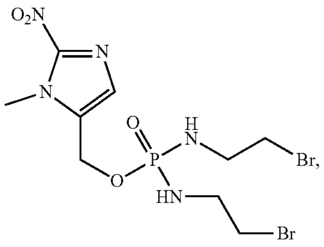

wherein active ingredient is the compound of formula I-1, solvent is composed of water and tert-butanol, the volume percentage of tert-butanol relative to the solution is in the range of 20-99%, and the content of the compound of formula I-1 in the solution is greater than 5 mg/ml and less than or equal to 160 mg/ml.

20. The solution according to claim 4, wherein the content of the compound of formula I in the solution is greater than or equal to 8 mg/ml and less than or equal to 50 mg/ml.

21. The solution according to claim 1, wherein the solution is used for preparing a lyophilized formulation with a high drug load, and comprises a compound of the following formula I-1, water, tert-butanol and sucrose, or a compound of the following formula I-1, water, tert-butanol and mannitol, (I-1)

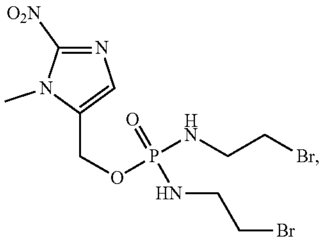

wherein active ingredient is the compound of formula I-1, solvent is composed of water and tert-butanol, the volume percentage of tert-butanol relative to the solution is in the range of 30-60% or the content of tert-butanol in the solution is in the range of 235.5-471 mg/ml, the content of the compound of formula I-1 in the solution is in the range of 6-25 mg/ml, sucrose or mannitol is used as an excipient, and the content of sucrose or mannitol in the solution is in the range of 40-100 mg/ml.

22. The solution according to claim 1, wherein the solution is used for preparing a lyophilized formulation with a high drug load, and comprises a compound of the following formula I-1, water, tert-butanol, sucrose, and a pH regulator, or a compound of the following formula I-1, water, tert-butanol, mannitol, and a pH regulator, (I-1)

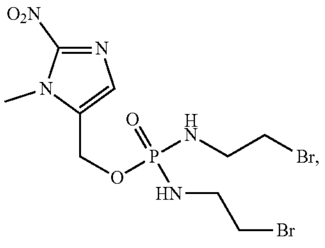

wherein active ingredient is the compound of formula I-1, solvent is composed of water and tert-butanol, the volume percentage of tert-butanol relative to the solution is in the range of 30-60% or the content of tert-butanol in the solution is in the range of 235.5-471 mg/ml, the content of the compound of formula I-1 in the solution is in the range of 6-25 mg/ml, sucrose or mannitol is used as an excipient, and the content of sucrose or mannitol in the solution is in the range of 40-100 mg/ml, and the content of the pH regulator is such that the pH value of the solution is in the range of 4-9.

23. The solution according to claim 22, wherein the pH regulator is sodium bicarbonate.

24. The lyophilized formulation according to claim 8, comprising a compound of the following formula I-1, an excipient, and residual solvent components, (I-1)

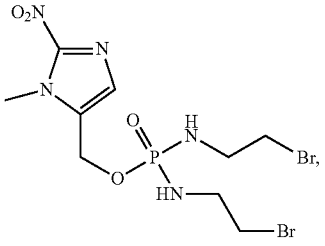

wherein active ingredient is the compound of formula I-1, the drug load of the compound of formula I-1 in the lyophilized formulation is greater than 5.55 mg/$cm^3$ and less than or equal to 177.77 mg/$cm^3$, and the residual solvent components are water and tert-butanol.

25. The lyophilized formulation according to claim 8, comprising a compound of the following formula I-1, an excipient, residual solvent components and a pH regulator, (I-1)

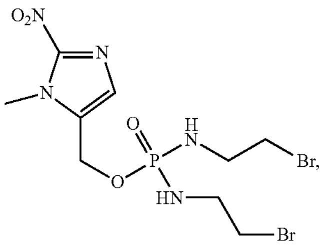

wherein active ingredient is the compound of formula I-1, the drug load of the compound of formula I-1 in the lyophilized formulation is greater than 5.55 mg/$cm^3$ and less than or equal to 177.77 mg/$cm^3$, and the residual solvent components are water and tert-butanol.

26. The lyophilized formulation according to claim 8, comprising a compound of the following formula I-1 and an excipient, (I-1)

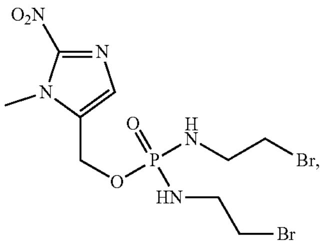

wherein active ingredient is the compound of formula I-1, the drug load of the compound of formula I-1 in the lyophilized formulation is greater than 5.55 mg/$cm^3$ and less than or equal to 177.77 mg/$cm^3$.

27. The lyophilized formulation according to claim 10, wherein the protein is selected from bovine serum albumin and human albumin.

28. The lyophilized formulation according to claim 11, wherein the residual water content is less than or equal to 2%.

29. The lyophilized formulation according to claim 11, wherein the residual tert-butanol content is less than or equal to 1%.

30. The lyophilized formulation according to claim 12, wherein the mass ratio of the compound of formula I and the excipient is 1: (1-15).

31. The lyophilized formulation according to claim 13, wherein the drug load of the compound of formula I in the lyophilized formulation is greater than or equal to 8.88 mg/cm$^3$ and less than or equal to 145.45 mg/cm$^3$.

32. The lyophilized formulation according to claim 13, wherein the drug load of the compound of formula I in the lyophilized formulation is greater than or equal to 8.88 mg/cm$^3$ and less than or equal to 27.77 mg/cm$^3$.

33. The lyophilized formulation according to claim 13, wherein the drug load of the compound of formula I in the lyophilized formulation is greater than or equal to 7.27 mg/cm$^3$ and less than or equal to 22.73 mg/cm$^3$.

34. The lyophilized formulation according to claim 14, wherein the residual water content is less than or equal to 2%.

35. The lyophilized formulation according to claim 14, wherein the residual tert-butanol content is less than or equal to 1%.

36. The lyophilized formulation according to claim 8, essentially consisting of the following compound I-1, an excipient, and residual water and residual tert-butanol, (I-1)

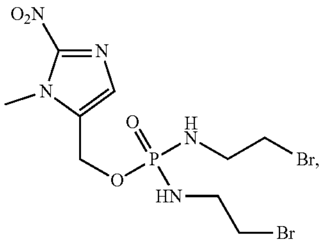

wherein the drug load of the compound of formula I-1 in the lyophilized formulation is 5.55-27.77 mg/cm$^3$;

the excipient is sucrose or mannitol;

the mass ratio of the compound of formula I-1 to the excipient is 1:2-1:9.375;

the residual water content is less than or equal to 6% by mass; and the residual tert-butanol content is less than or equal to 1.75% by mass.

37. The lyophilized formulation according to claim 8, essentially consisting of the following compound I-1, an excipient, and residual water and residual tert-butanol, and a pH regulator, (I-1)

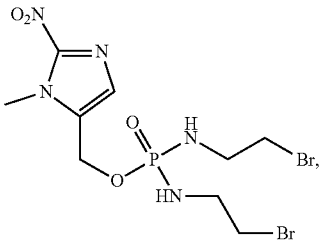

wherein the drug load of the compound of formula I-1 in the lyophilized formulation is 5.55-27.77 mg/cm$^3$;

the excipient is sucrose or mannitol;

the mass ratio of the compound of formula I-1 to the excipient is 1:2-1:9.375;

the residual water content is less than or equal to 6% by mass;

the residual tert-butanol content is less than or equal to 1.75% by mass; and the pH regulator is sodium bicarbonate, and its content is in the range of 0.01-0.10 mg/cm$^3$.

38. The lyophilized formulation according to claim 8, essentially consisting of the following compound I-1 and an excipient, (I-1)

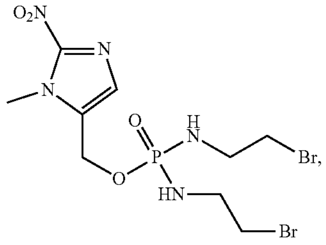

wherein the drug load of the compound of formula I-1 in the lyophilized formulation is 5.55-27.77 mg/cm$^3$;

the excipient is sucrose or mannitol; and the mass ratio of the compound of formula I-1 to the excipient is 1:2-1:9.375.

39. The unit package containing the lyophilized formulation according to claim 15, which has the following characteristics:

the lyophilized formulation is contained in a sealed container with a capacity of 100 ml;

the volume of the lyophilized formulation is from ⅓ to ½ of the volume of the sealed container, and the amount of the compound of formula I is in the range of 400-2000 mg; or the lyophilized formulation is contained in a sealed container with a capacity of 50 ml;

the volume of the lyophilized formulation is from ⅓ to ½ of the volume of the sealed container, and the amount of the compound of formula I is in the range of 50-800 mg; or the lyophilized formulation is contained in a sealed container with a capacity of 30 ml; the volume of the lyophilized formulation is from ⅓ to ½ of the volume of the sealed container, and the content of the compound of formula I is in the range of 150-600 mg; or the lyophilized formulation is contained in a sealed container with a capacity of 25 ml; the volume of the lyophilized formulation is from ⅓ to ½ of the volume of the sealed container, and the amount of the compound of formula I is in the range 125-500 mg; or the lyophilized formulation is contained in a sealed container with a capacity of 20 ml; the volume of the lyophilized formulation is from ⅓ to ½ of the volume of the sealed container, and the amount of the compound of formula I is in the range of 100-400 mg; or the lyophilized formulation is contained in a sealed container with a capacity of 18 ml; the volume of the lyophilized formulation is from ⅓ to ½ of the volume of the sealed container, and the amount of the compound of formula I is in the range of 90-360 mg; or the lyophilized formulation is contained in a sealed container with a capacity of 15 ml; the volume of the lyophilized formulation is from ⅓ to ½ of the volume of the sealed container, and the amount of the compound of formula I is in the range of 75-300 mg; or the lyophilized formulation is contained in a sealed container with a capacity of 10 ml; the volume of the lyophilized formulation is from ⅓ to ½ of the volume of the sealed container, and the amount of the compound of formula I is in the range of 50-200 mg; or the lyophilized formulation is contained in a sealed container with a capacity of 8 ml; the volume of the lyophilized formulation is from ⅓ to ½ of the volume of the sealed container, and the amount of the compound of formula I is in the range of 40-160 mg; or the lyophilized formulation is contained in a sealed container with a capacity of 7 ml; the volume of the lyophilized formulation is from ⅓ to ½ of the volume of the sealed container, and the amount of the compound of formula I is in the range of 35-140 mg; or the lyophilized formulation is contained in a sealed container with a capacity of 5 ml; the volume of the lyophilized formulation is from ⅓ to ½ of the volume of the sealed container, and the amount of the compound of formula I is in the range of 25-100 mg.

40. The method according to claim 17, comprising the following procedures:

Procedure 1: the prescribed amount of the active pharmaceutical ingredient TH-302 was weighed, added into an aqueous tert-butanol solution, and stirred until it was clear to obtain a first solution;

Procedure 2: the prescribed amount of mannitol or sucrose was dissolved in an appropriate amount of water, stirred until it was clear to obtain a second solution;

Procedure 3: the first solution and the second solution were mixed, and finally added with the remaining prescribed amount of tert-butanol, and then added an appropriate amount of water to the predetermined volume, and further added the prescribed amount of sodium bicarbonate, and mixed homogenously under stirring;

wherein the content of the active pharmaceutical ingredient TH-302 in the solution of the lyophilized formulation with a high drug load is greater than 5 mg/ml and less than or equal to 160 mg/ml;

the volume percentage of tert-butanol relative to the solution of the lyophilized formulation with a high drug load is in the range of 30-90%, the content of sucrose or mannitol in the solution of the lyophilized formulation with a high drug load is in the range of 20-300 mg/ml;

the mass ratio of TH-302 to sucrose or mannitol in the solution of the lyophilized formulation with a high drug load is in the range of 1: (0.5-20);

the volume ratio of tert-butanol in the aqueous tert-butanol solution is in the range of 30-90%; and the content of sodium bicarbonate in the solution of the lyophilized formulation with a high drug load is in the range of 0.01-0.10 mg/ml.

* * * * *